United States Patent
Angibaud et al.

(10) Patent No.: US 8,403,934 B2
(45) Date of Patent: Mar. 26, 2013

(54) ALIGNMENT GUIDES FOR USE IN COMPUTER ASSISTED ORTHOPEDIC SURGERY TO PREPARE A BONE ELEMENT FOR AN IMPLANT

(75) Inventors: Laurent Angibaud, Gainesville, FL (US); C. Michael Mauldin, Lake City, FL (US); Anthony Boyer, Echirolles (FR); Stéphane Lavallee, Saint Martin d'uriage (FR)

(73) Assignees: Exactech Inc., Gainesville, FL (US); Blue Ortho, La Tronche (FR)

( * ) Notice: Subject to any disclaimer, the term of this patent is extended or adjusted under 35 U.S.C. 154(b) by 281 days.

(21) Appl. No.: 12/879,134

(22) Filed: Sep. 10, 2010

(65) Prior Publication Data

US 2011/0060341 A1    Mar. 10, 2011

Related U.S. Application Data

(60) Provisional application No. 61/241,269, filed on Sep. 10, 2009.

(51) Int. Cl.
   *A61B 17/58* (2006.01)
   *A61B 17/60* (2006.01)
   *A61F 2/00* (2006.01)

(52) U.S. Cl. ............................ 606/88; 606/87; 606/89

(58) Field of Classification Search ............ 606/87–89
   See application file for complete search history.

(56) References Cited

U.S. PATENT DOCUMENTS

| | | |
|---|---|---|
| 5,735,856 A | 4/1998 | McCue et al. |
| 5,799,055 A | 8/1998 | Peshkin et al. |
| 5,880,976 A | 3/1999 | DiGioia, III et al. |
| 6,002,859 A | 12/1999 | DiGioia, III et al. |
| 6,069,932 A | 5/2000 | Peshkin et al. |
| 6,198,794 B1 | 3/2001 | Peshkin et al. |
| 6,205,411 B1 | 3/2001 | DiGioia, III et al. |
| 6,258,096 B1 | 7/2001 | Seki |
| 6,514,259 B2 | 2/2003 | Picard et al. |
| 6,595,997 B2 | 7/2003 | Axelson, Jr. et al. |
| 6,611,141 B1 | 8/2003 | Schulz et al. |
| 6,685,711 B2 | 2/2004 | Axelson, Jr. et al. |
| 6,711,431 B2 | 3/2004 | Sarin et al. |
| 6,827,723 B2 | 12/2004 | Carson |

(Continued)

FOREIGN PATENT DOCUMENTS

| | | |
|---|---|---|
| WO | 2006/106419 | 10/2006 |
| WO | 2010/046455 | 4/2010 |

OTHER PUBLICATIONS

International Search Report from corresponding International Application No. PCT/US10/48346 mailed Nov. 5, 2010.

(Continued)

*Primary Examiner* — Sameh Boles
(74) *Attorney, Agent, or Firm* — Greenberg Traurig, LLP

(57) ABSTRACT

In an embodiment, the methodology of the present invention is based on the use of an intraoperative navigation system and of a compact alignment guide for alignment of implant components. In an embodiment, an alignment guide of the present invention includes a first component fixable to a bone element; a second mobile component, and a third mobile component, wherein the second mobile component and two control mechanisms form a first link, wherein the two control mechanisms are working in parallel to perform adjustments in two degrees of freedom, wherein the third mobile component and three control mechanisms form a second link, wherein the three control mechanisms are working in parallel to perform adjustments in three additional degrees of freedom, and wherein the first link adjustments and the second link adjustments are performed in series to provide a total adjustment of five degrees of freedom relative to the first component.

13 Claims, 17 Drawing Sheets

U.S. PATENT DOCUMENTS

| | | |
|---|---|---|
| 6,856,828 B2 | 2/2005 | Cossette et al. |
| 6,859,661 B2 | 2/2005 | Tuke |
| 6,923,817 B2 | 8/2005 | Carson et al. |
| 6,993,374 B2 | 1/2006 | Sasso |
| 7,008,430 B2 | 3/2006 | Dong et al. |
| RE39,133 E | 6/2006 | Clayton et al. |
| 7,104,997 B2 | 9/2006 | Lionberger et al. |
| 7,182,767 B2 | 2/2007 | Canonaco et al. |
| 7,217,276 B2 | 5/2007 | Henderson et al. |
| 7,237,556 B2 | 7/2007 | Smothers et al. |
| 7,241,298 B2 | 7/2007 | Nemec et al. |
| 7,309,339 B2 | 12/2007 | Cusick et al. |
| RE40,176 E | 3/2008 | Peshkin et al. |
| 7,364,581 B2 | 4/2008 | Michalowicz |
| 7,377,924 B2 | 5/2008 | Raistrick et al. |
| 7,412,777 B2 | 8/2008 | Pelletier et al. |
| 7,427,200 B2 | 9/2008 | Noble et al. |
| 7,427,272 B2 | 9/2008 | Richard et al. |
| 7,442,196 B2 | 10/2008 | Fisher et al. |
| 7,477,926 B2 | 1/2009 | McCombs |
| 7,488,324 B1 | 2/2009 | Metzger et al. |
| 7,534,263 B2 | 5/2009 | Burdulis, Jr. et al. |
| 7,542,791 B2 | 6/2009 | Mire et al. |
| 7,547,307 B2 | 6/2009 | Carson et al. |
| 7,736,368 B2 | 6/2010 | Couture et al. |
| 7,744,600 B2 | 6/2010 | Rangaiah et al. |
| 2005/0149041 A1* | 7/2005 | McGinley et al. ............ 606/88 |
| 2005/0171545 A1 | 8/2005 | Walsh et al. |
| 2008/0195109 A1 | 8/2008 | Hunter et al. |
| 2010/0191244 A1 | 7/2010 | White et al. |

OTHER PUBLICATIONS

Inkpen, K. "Precision and Accuracy in Computer-Assisted Total Knee Replacement", The University of British Columbia, Dec. 1999.
"Praxim: Nanoblock®—Easy to Use, Precise, Save Time", © 2010 Praxim http://www.praxim.fr/Products_22.html; first viewed online 2008.

* cited by examiner

ALIGNMENT GUIDES FOR USE IN COMPUTER ASSISTED ORTHOPEDIC SURGERY TO PREPARE A BONE ELEMENT FOR AN IMPLANT

RELATED APPLICATIONS

This application claims the benefit of and priority to U.S. Provisional Application Ser. No. 61/241,269, filed Sep. 10, 2009, the entirety of this application is hereby incorporated herein by reference.

BACKGROUND

Total knee arthroplasty (TKA) is one of the most clinically successful and cost-effective interventions in health care, with numerous investigators reporting excellent long-term results in terms of reducing pain, improving function, and increasing quality of life in patients. Among the many factors that influence TKA outcomes, surgical technique and final prosthesis alignment appear the most critical. It is known that an accurate restoration of the overall lower limb alignment reduces polyethylene wear and therefore the risk of aseptic loosening. Furthermore, errors in varus/valgus alignment greater than 3 degrees for the femoral or tibial component have been shown to result in less satisfactory clinical outcomes and a higher risk of loosening. Also, malrotation in the transverse plane of the femoral or tibial components has been shown to affect correct function of the extensor mechanism of the replaced knee, which may lead to anterior knee pain. The elevation of the joint line limits the range of motion of the knee. Finally, instability, malalignment, and/or malposition are the major reasons for TKA revision and, except for infection, are all related to incorrect surgical technique. Although various guides for alignment have been designed to improve accuracy, several limitations remain.

Computer Assisted Orthopedic Surgery (CAOS) is a discipline where computer technology is applied pre-, intra- and/or post-operatively to improve the outcome of orthopedic surgical procedures. The principal idea behind CAOS is that operative outcomes will be improved through the use of computer technology. Taking the example of joint replacement, the task of the surgeon is to integrate the new joint components into the patient's existing anatomy. CAOS technologies allow the surgeon to: plan the component placement in advance, including determination of the appropriate component sizes; measure the intra-operative placement of the components in real time, making sure that the plan is adhered to; and measure the post-operative result.

SUMMARY

Alignment guides for use in computer assisted orthopedic surgery to prepare a bone element for an implant are disclosed herein. In an embodiment, the methodology of the present invention is based on the use of an intraoperative navigation system and of a reduced and compact alignment guide for alignment of implant components.

According to an embodiment of the present invention, there is disclosed an alignment guide for preparing a bone element for receiving an implant that includes a first component fixable to the bone element, wherein the first component serves as a fixed rigid body; and a second component moveable with respect to the first component and having at least one guide that accommodates a surgical instrument, wherein the second component and two control mechanisms form a first link, wherein the two control mechanisms are working in parallel to perform adjustments in up to two degrees of freedom so as to result in up to two degrees of freedom alignment of the at least one guide for preparing the bone element for the implant.

According to an embodiment of the present invention, there is disclosed an alignment guide for preparing a bone element for receiving an implant that includes a first component fixable to the bone element comprising a first bore that accommodates a first ball head fastener; and a second bore that accommodates a second ball head fastener, wherein the first component serves as a fixed rigid body; and a second component moveable with respect to the first component comprising a first ball socket that accommodates a first ball of the first ball head fastener; a second ball socket that accommodates a second ball of the second ball head fastener; and at least one guide that accommodates a surgical instrument, wherein the first ball head fastener and the second ball head fastener are working in parallel to perform adjustments in up to two degrees of freedom so as to result in up to two degrees of freedom alignment of the at least one guide for preparing the bone element for the implant.

According to an embodiment of the present invention, there is disclosed an alignment guide for preparing a bone element for receiving an implant that includes a first component fixable to the bone element, wherein the first component serves as a fixed rigid body; a second component moveable with respect to the first component; and a third component moveable with respect to the second component and the first component, the third component comprising at least one guide that accommodates a surgical instrument, wherein the second component and n control mechanisms form a first link, wherein n control mechanisms are working in parallel to perform adjustments in up to n degrees of freedom of the alignment guide so as to result in up to n degrees of freedom alignment of the at least one guide for preparing the bone element for the implant, wherein the third component and m control mechanisms form a second link, wherein m control mechanisms are working in parallel to perform adjustments in up to m additional degrees of freedom of the alignment guide so as to result in up to m additional degrees of freedom alignment of the at least one guide for preparing the bone element for the implant, and wherein a total degree of freedom adjustment of the at least one guide relative to the first component is up to n+m degrees of freedom.

According to aspects illustrated herein, there is disclosed an alignment guide for preparing a bone element for receiving an implant that includes a first component fixable to the bone element comprising a first bore that accommodates a first ball head fastener; and a second bore that accommodates a second ball head fastener, wherein the first component serves as a fixed rigid body; a second component moveable with respect to the first component comprising a first ball socket that accommodates a first ball of the first ball head fastener; a second ball socket that accommodates a second ball of the second ball head fastener; a third ball socket that accommodates a third ball of a third ball head fastener; a fourth ball socket that accommodates a fourth ball of a fourth ball head fastener; and a fifth ball socket that accommodates a fifth ball of a fifth ball head fastener; and a third component moveable with respect to the second component and the first component comprising a third bore that accommodates the third ball head fastener; a fourth bore that accommodates the fourth ball head fastener; a fifth bore that accommodates the fifth ball head fastener; and at least one guide that accommodates a surgical instrument, wherein the first ball head fastener and the second ball head fastener are working in parallel to perform adjustments in up to two degrees of freedom so as to result in up to two degrees of freedom alignment of the at least one guide for preparing the bone element for the implant, wherein the third ball head fastener, the fourth ball head fastener and the fifth ball head fastener are working in parallel to perform adjustments in up to three additional degrees of freedom so as to result in up to three additional degrees of freedom alignment of the at least one guide for preparing the bone element for the implant, and wherein a total degree of freedom adjustment of the at least one guide relative to the first component is up to five degrees of freedom.

According to aspects illustrated herein, there is disclosed a method of preparing a femur for receiving an implant that includes fixing a first component of an alignment guide to distal condyles of the femur; tracking orientation and relative displacement of a second component of the alignment guide with respect to the first component using a mobile navigation tracker; controlling up to n degrees of freedom of the alignment guide by parallel adjustment of the second component relative to the first component to position the second component in a desired position relative to the femur; tracking orientation and relative displacement of a third component of the alignment guide with respect to the second component and the first component using the mobile navigation tracker; controlling up to m additional degrees of freedom of the alignment guide by parallel adjustment of the third component relative to the second component and the first component to position the third component in a desired position relative to the femur; forming at least one hole on a femoral cortex of the femur using a drill bit or similar means; maintaining the drill bit on the femoral cortex so as to serve as a fixation means; forming at least one hole on the distal condyles of the femur; removing the alignment guide from the femur; positioning a cutting block attachable to the fixation means on the femoral cortex; performing a distal femoral resection using the cutting block as a guide; removing the cutting block from the anterior femoral cortex; positioning a cutting block on the distal condyles based on the hole formed on the distal condyles; and completing resection of the femur for receiving the implant.

BRIEF DESCRIPTION OF THE DRAWINGS

The present invention will be further explained with reference to the attached drawings, wherein like structures are referred to by like numerals throughout the several views. The drawings shown are not necessarily to scale, with emphasis instead generally being placed upon illustrating the principles of the present invention.

Figure 1A:
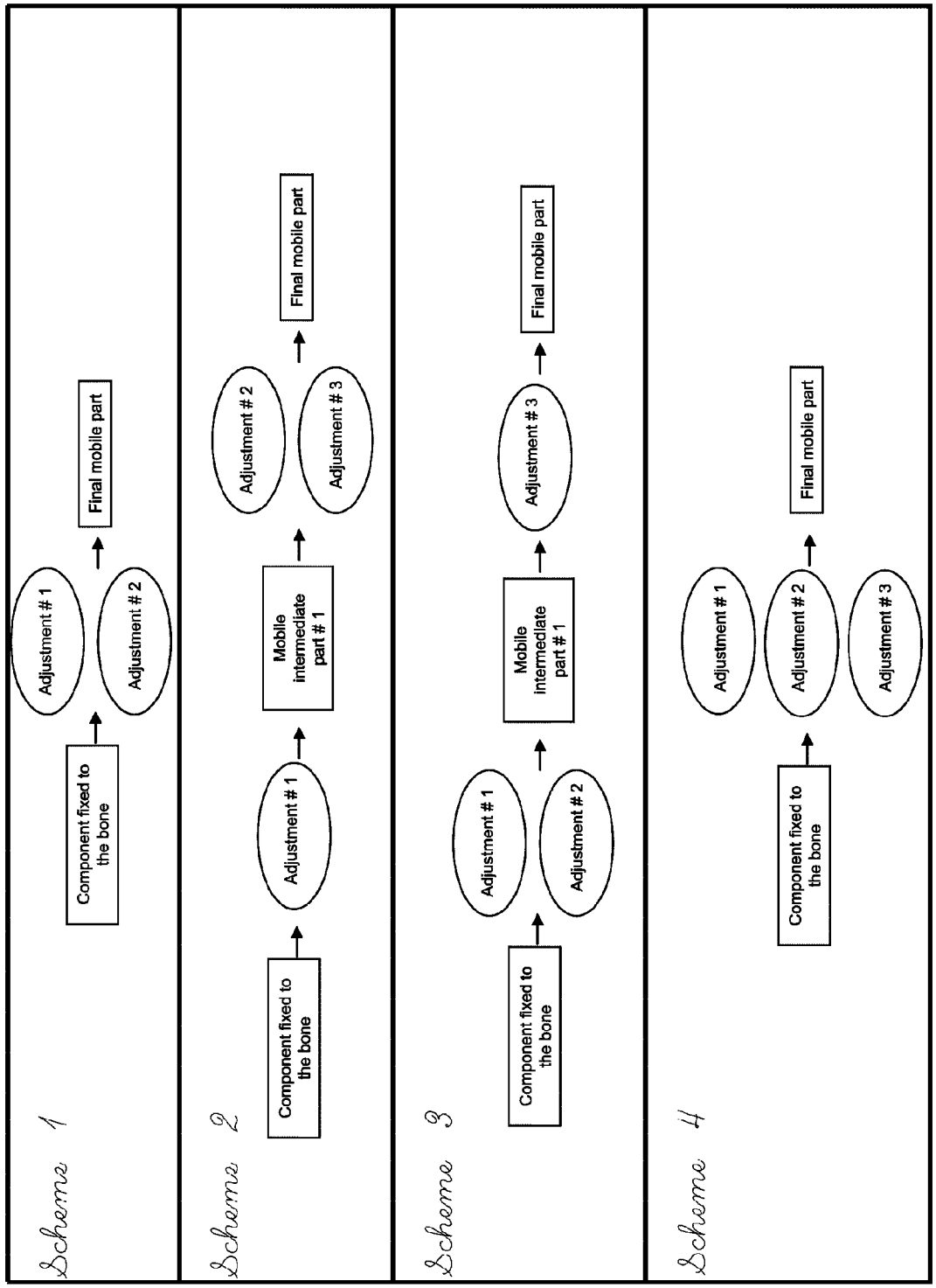
FIG. 1A, schemes 1-4, are flow charts showing various embodiments of parallel manipulator structures having a closed kinematic chain, wherein at least two control mechanisms are working in parallel to perform adjustments in two degrees of freedom. An alignment guide of the present invention can have a structure as shown in schemes 1-4.
Figure 1B:
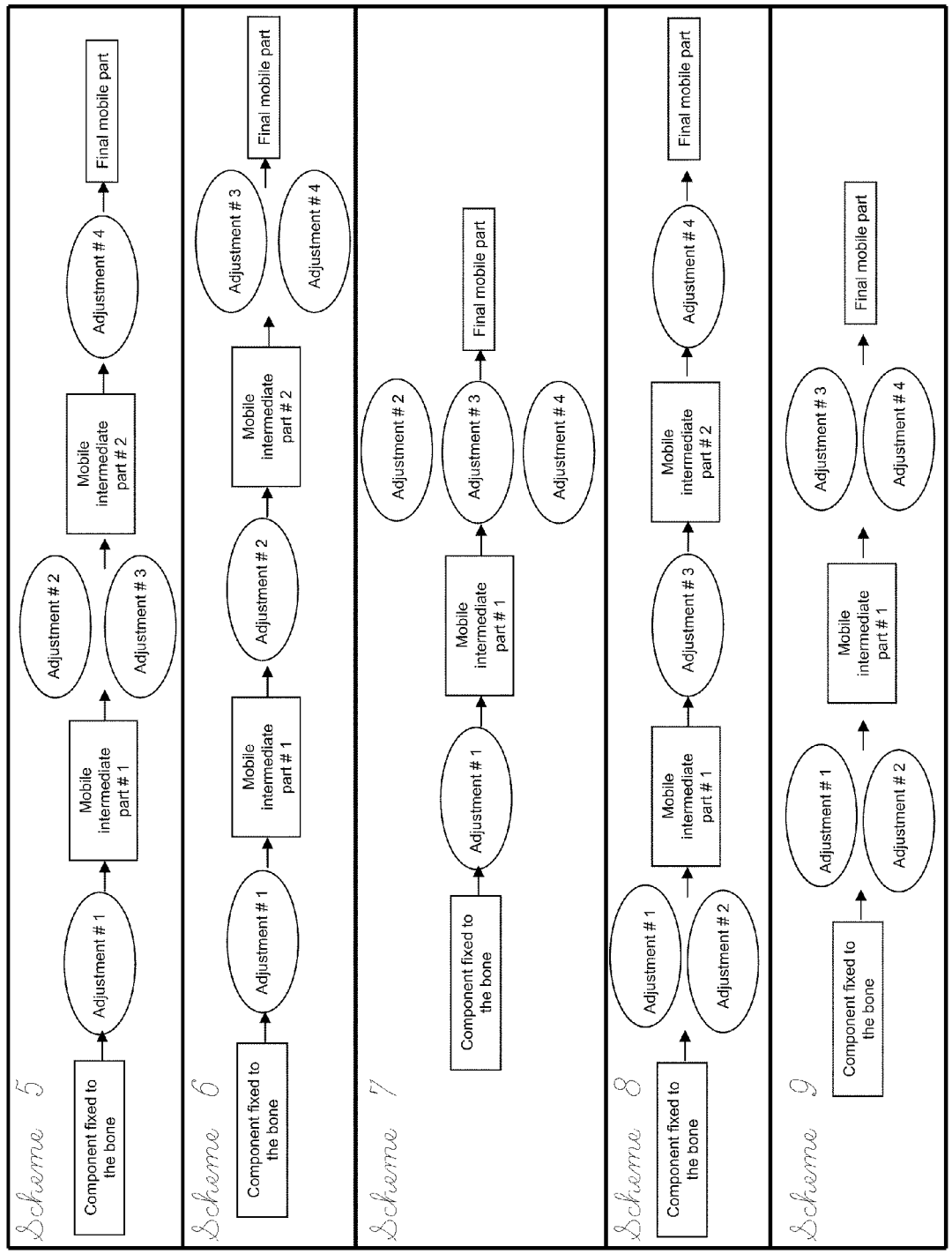
FIG. 1B, schemes 5-9, are flow charts showing various embodiments of parallel manipulator structures having a closed kinematic chain, wherein at least two control mechanisms are working in parallel to perform adjustments in two degrees of freedom. An alignment guide of the present invention can have a structure as shown in schemes 5-9.
Figure 1C:
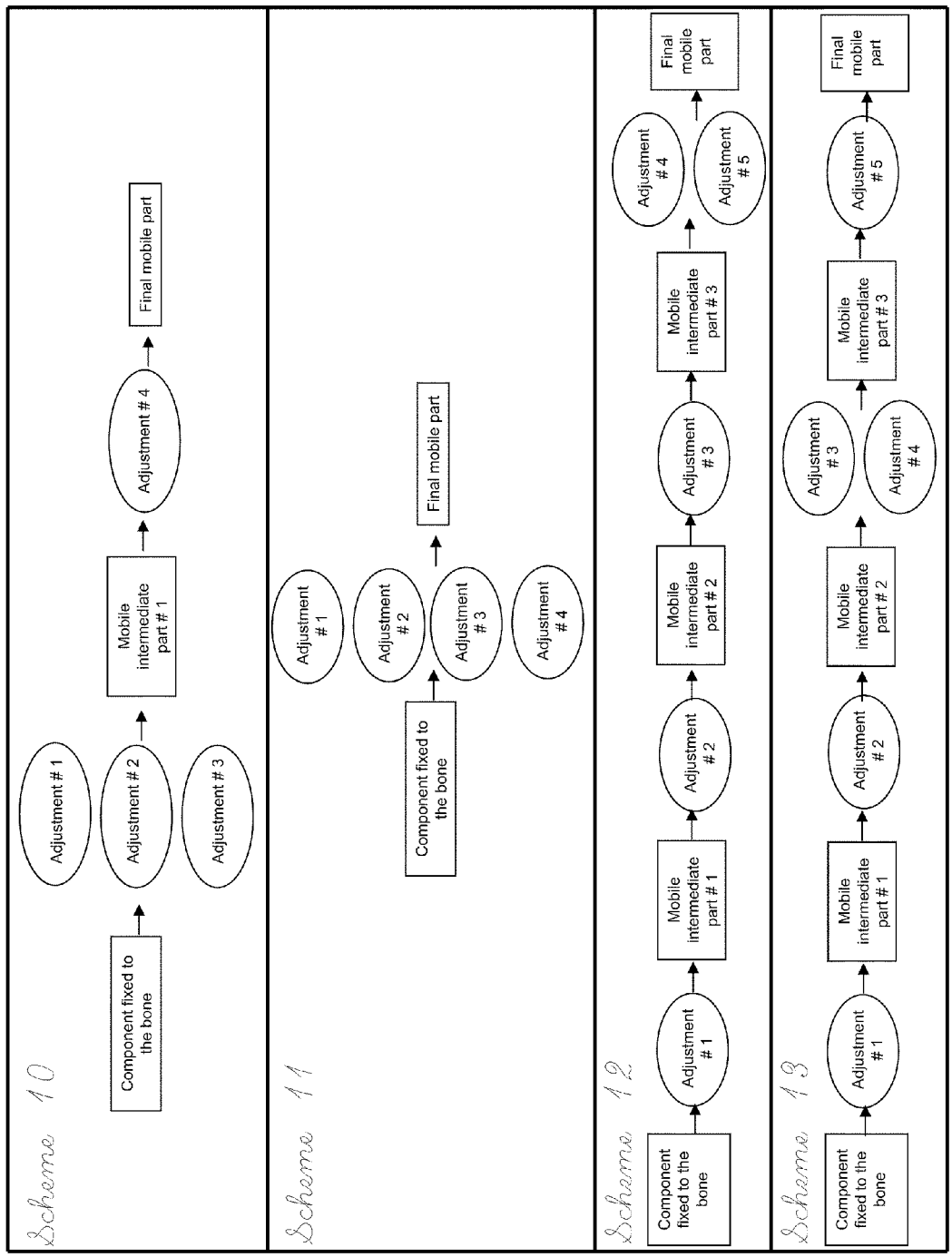
FIG. 1C, schemes 10-13, are flow charts showing various embodiments of parallel manipulator structures having a closed kinematic chain, wherein at least two control mechanisms are working in parallel to perform adjustments in two degrees of freedom. An alignment guide of the present invention can have a structure as shown in schemes 10-13.
Figure 1D:
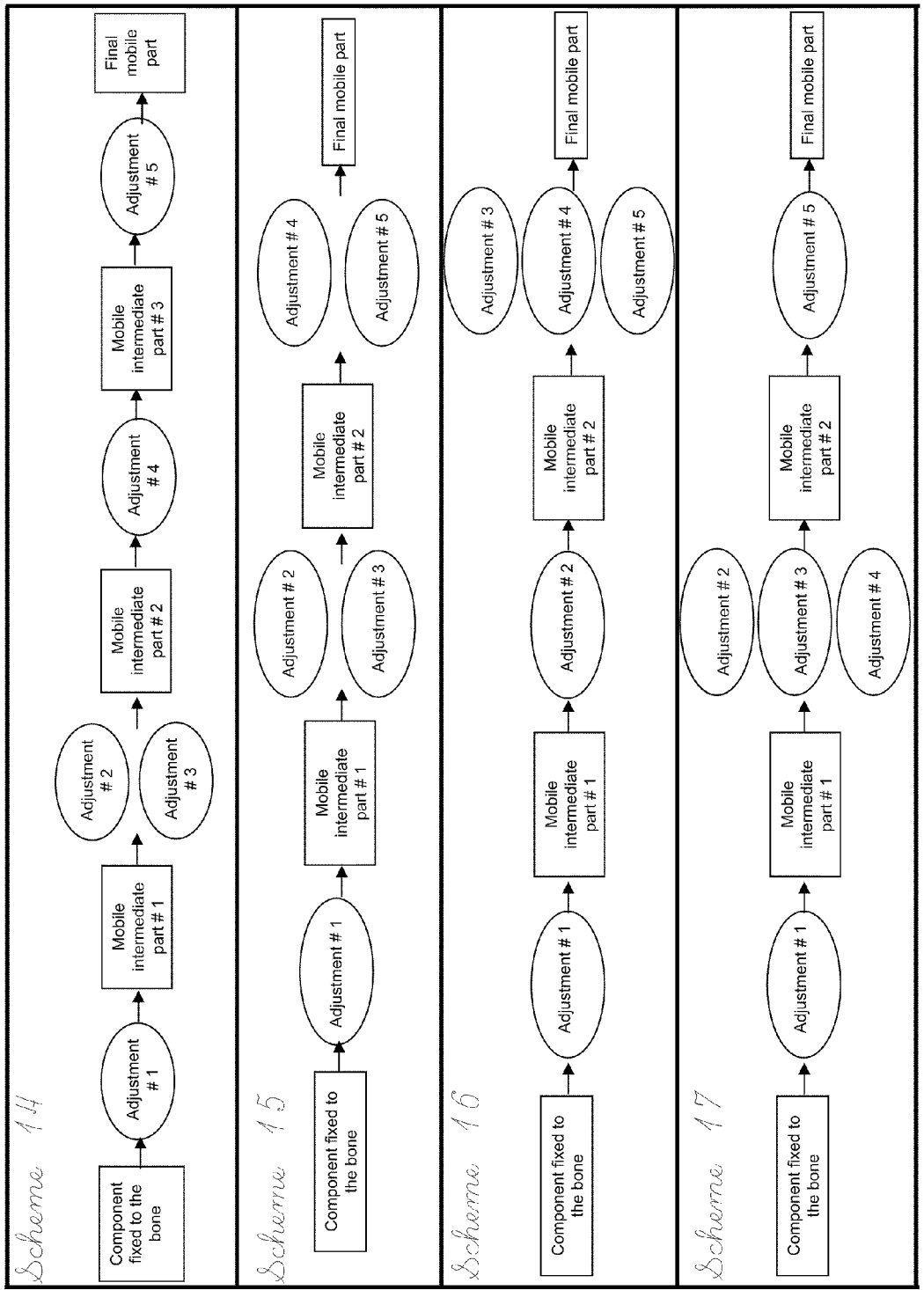
FIG. 1D, schemes 14-17, are flow charts showing various embodiments of parallel manipulator structures having a closed kinematic chain, wherein at least two control mechanisms are working in parallel to perform adjustments in two degrees of freedom. An alignment guide of the present invention can have a structure as shown in schemes 14-17.
Figure 1E:
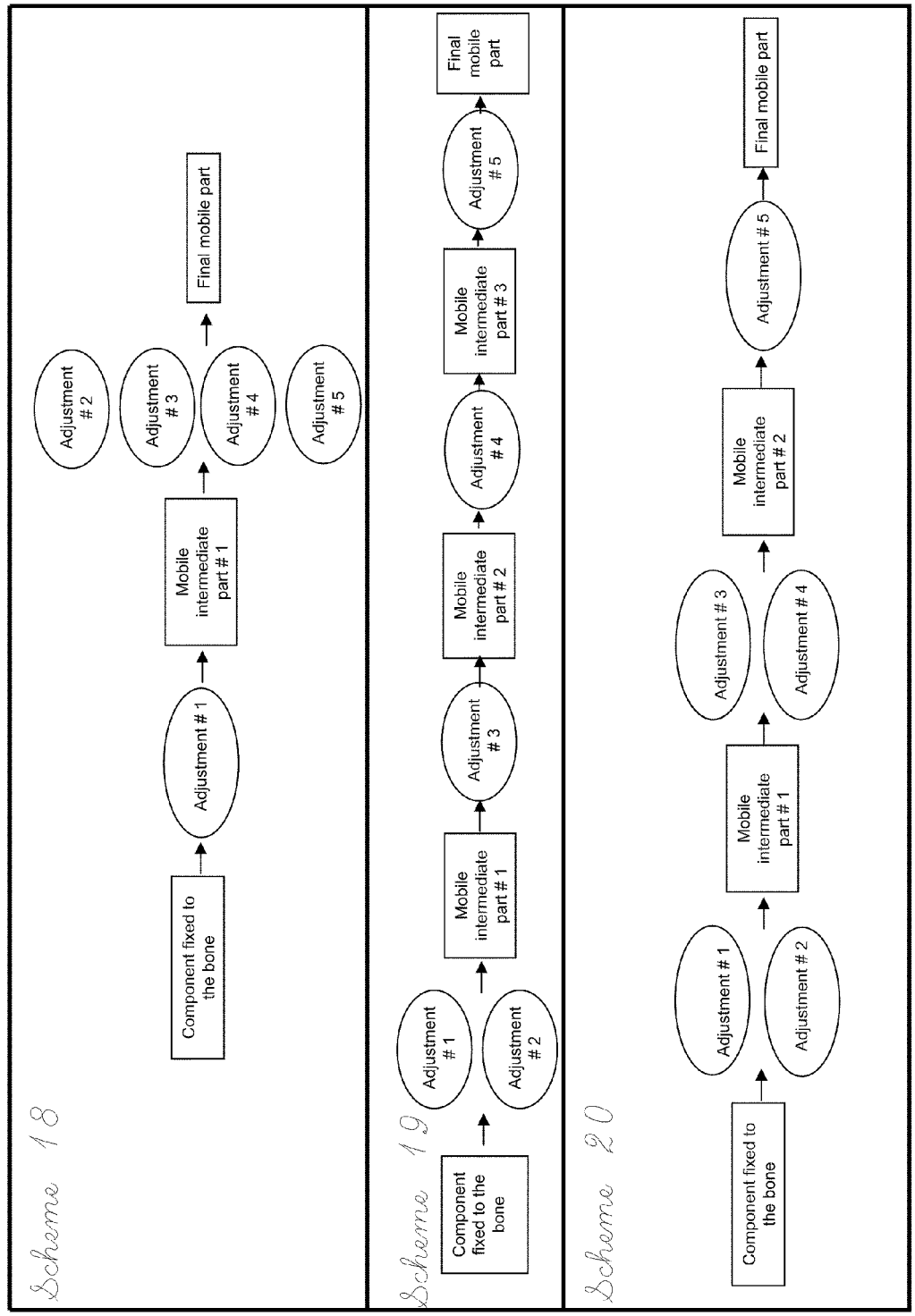
FIG. 1E, schemes 18-20, are flow charts showing various embodiments of parallel manipulator structures having a closed kinematic chain, wherein at least two control mechanisms are working in parallel to perform adjustments in two degrees of freedom. An alignment guide of the present invention can have a structure as shown in schemes 18-20.
Figure 1F:
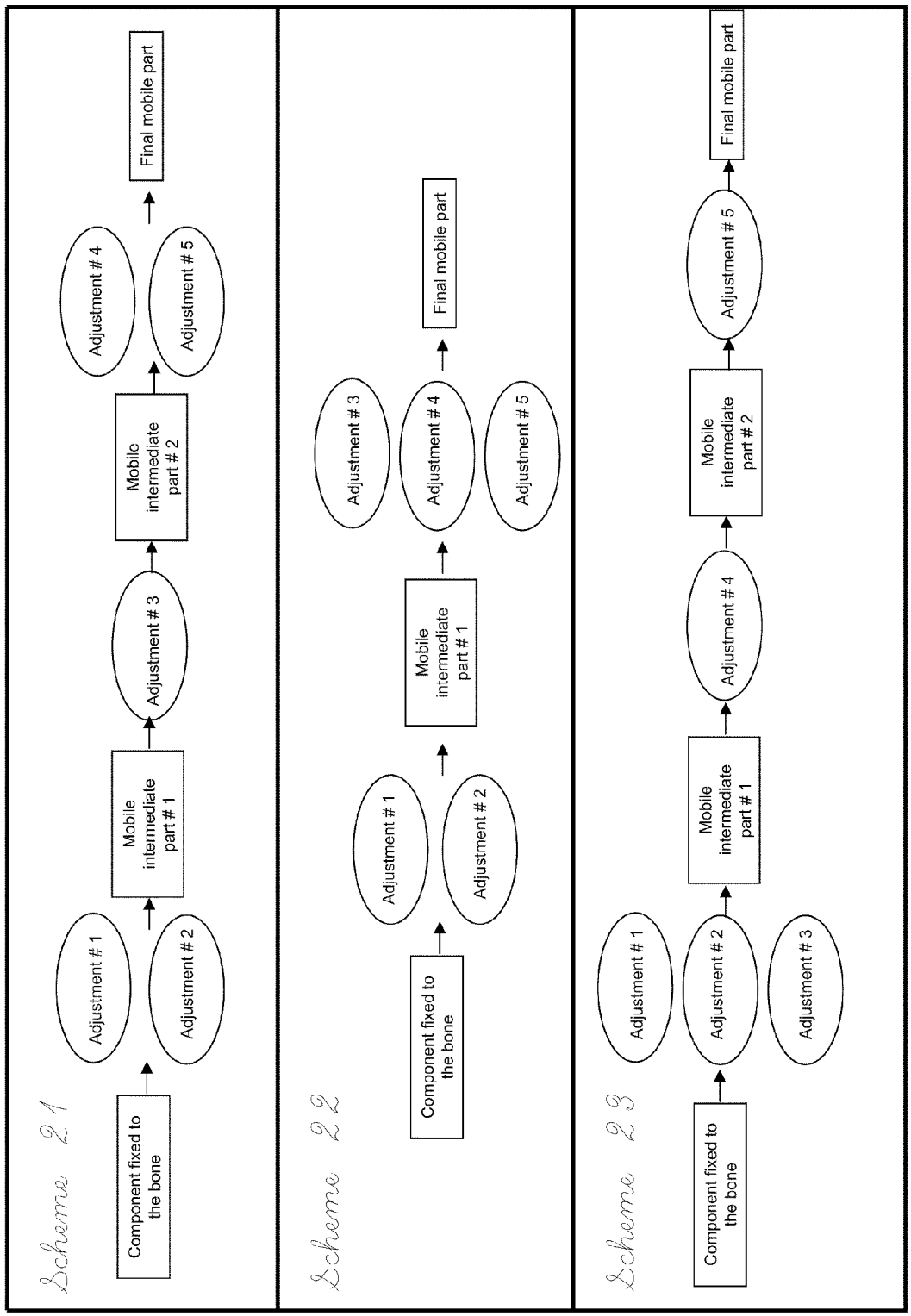
FIG. 1F, schemes 21-23, are flow charts showing various embodiments of parallel manipulator structures having a closed kinematic chain, wherein at least two control mechanisms are working in parallel to perform adjustments in two degrees of freedom. An alignment guide of the present invention can have a structure as shown in schemes 21-23.
Figure 1G:
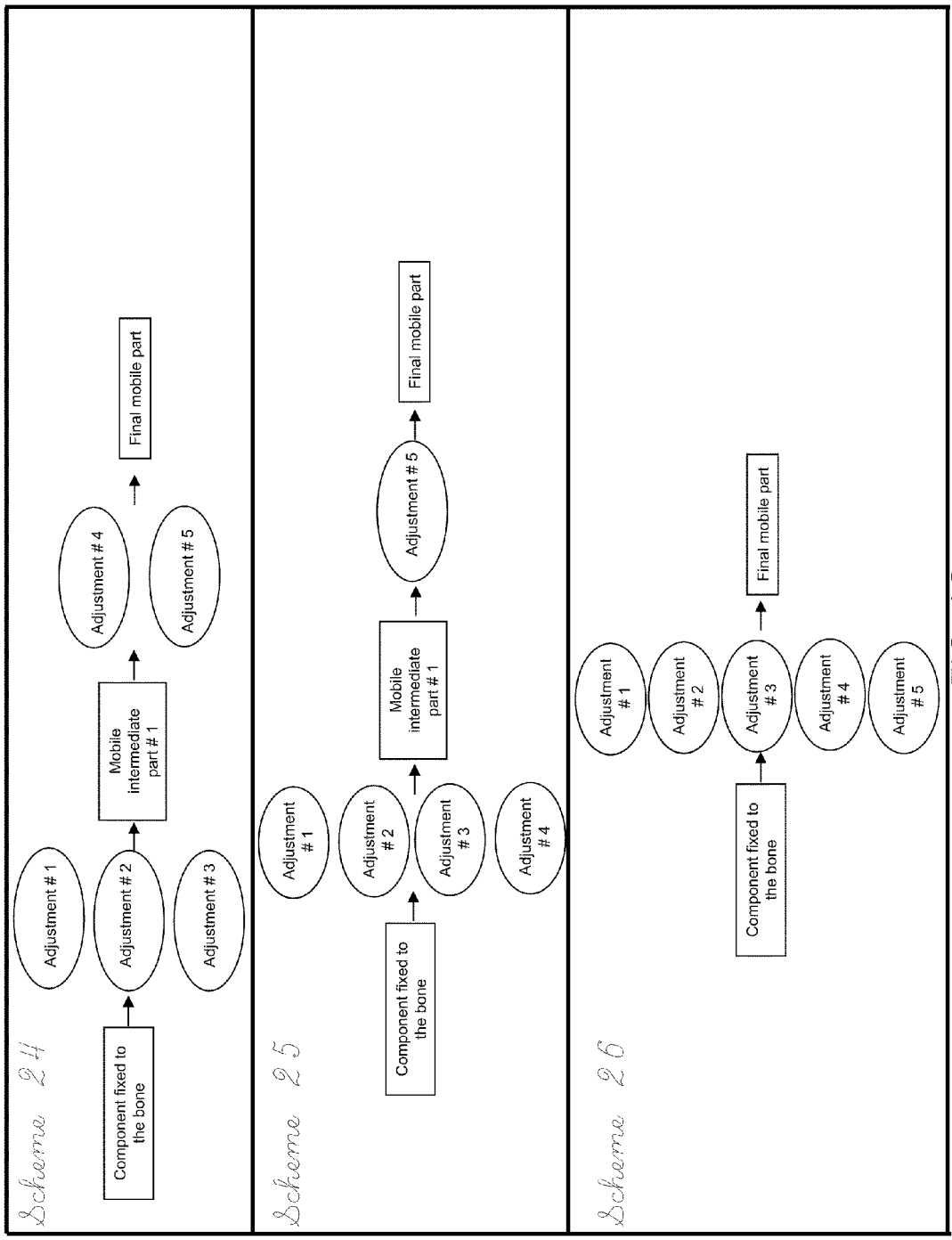
FIG. 1G, schemes 24-26, are flow charts showing various embodiments of parallel manipulator structures having a closed kinematic chain, wherein at least two control mechanisms are working in parallel to perform adjustments in two degrees of freedom. An alignment guide of the present invention can have a structure as shown in schemes 24-26.
Figure 1H:
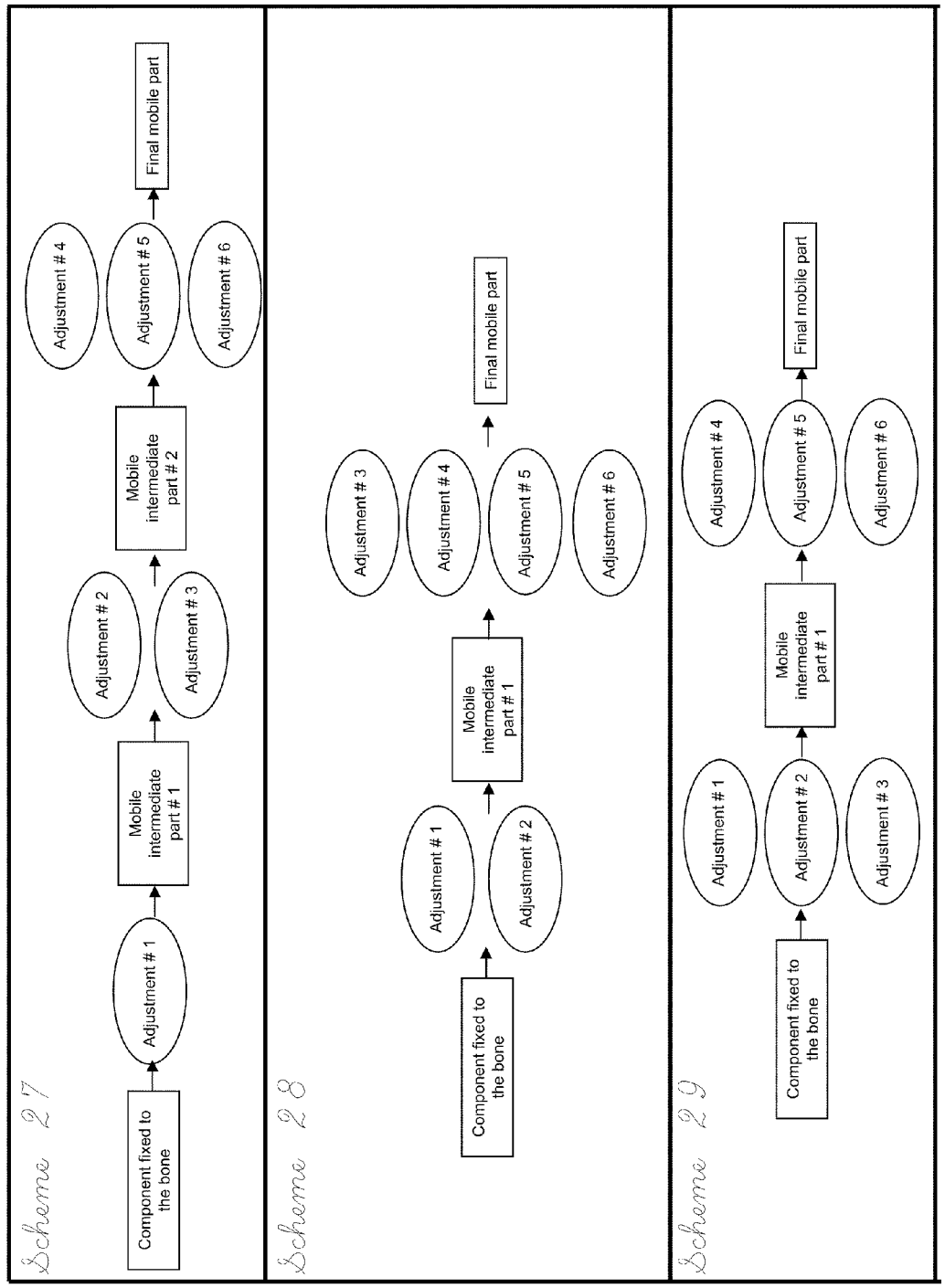
FIG. 1H, schemes 27-29, are flow charts showing various embodiments of parallel manipulator structures having a closed kinematic chain, wherein at least two control mechanisms are working in parallel to perform adjustments in two degrees of freedom. An alignment guide of the present invention can have a structure as shown in schemes 27-29.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed invention.

DETAILED DESCRIPTION

Computer technology has been introduced to assist in more accurate positioning of prosthetic components, allowing the surgeons to make informed decisions intraoperatively for precise prosthetic placement. Computer-assisted knee replacement surgery gives orthopaedic surgeons greater ability to perform less invasive procedures due to the enhanced surgical visualization. In CAOS, a data processor is used to receive and deliver data to assist the surgeon in making the best decisions. A three dimensional (3D) representation of the patient's knee is created by entering in patient data. Software will generate a digital model of each patient's knee joint.

Additionally, the software can provide detailed data relating to the bones and surrounding soft tissues. In some cases, there is no need for either X-rays or CT scans. This benefits the patient since no radiation exposure is involved. A technology is applied to produce a moving digital image of the patient's joint as it is moved during the operation. CAOS is incorporated with software to process representations real time. A digital model is produced that serves as a map for each particular procedure. The representation is then made available to surgeons to guide them through the operation. Surgical instruments can be incorporated into the map so that instrument position and progress can be monitored and controlled to within fractions of millimeters and degrees. Surgeons can use this real-time data to correct the procedure intraoperatively.

In an embodiment, the methodology of the present invention is based on the use of an intraoperative navigation system and of a reduced and compact alignment guide for alignment of implant components. In an embodiment, an alignment guide of the present invention is used to augment drill bit stabilization for improved drilling accuracy, which may have particular importance when using navigation systems to drill into small anatomic confines. In an embodiment, an intraoperative navigation system for use with an alignment guide of the present invention includes a computer for running the navigation system (for example, a central control unit with a 3D graphics board) and sensing devices used to track objects to reproduce their movements in virtual scenary. In an embodiment, the methodology of the present invention includes a measurement process for collecting patient-specific medical data, a decision making process for generating a surgical plan, a registration process for aligning the surgical plan to the patient, and an action process for accurately achieving the goals specified in the plan. In order to guide the surgeon towards correct placement of prosthetic components, the accurate and precise location of hole placement relative to the patient's anatomy can be tracked by intraoperative sensing devices and the required placement can be visually communicated to the surgeon on a video monitor. In an embodiment, one sensing device can be directly or indirectly fastened to the femur, one sensing device can be fastened to the tibia, and additional sensing device(s) can be fastened to a mobile component of an alignment guide of the present invention. In an embodiment, the navigation system software includes a registration module, a tracking module and a graphical human-machine interface.

In an embodiment, an alignment guide of the present invention provides guidance to a surgeon during a computer assisted TKA while preparing bone cuts. In an embodiment, an alignment guide of the present invention provides guidance to a surgeon during a computer assisted TKA to reduce the number of outliers while maintaining an ease of use. In an embodiment, an alignment guide of the present invention provides guidance to a surgeon during a computer assisted TKA to allow for intra-operative adjustment of one or a multitude of anatomical parameters.

In an embodiment, an alignment guide of the present invention is a five degree-of-freedom parallel manipulator made up of a fixed support or base plate connected to an end effector platform having guides by means of a number of "legs". In an embodiment, an alignment guide of the present invention is a five degree-of-freedom parallel manipulator that is a closed-loop kinematic chain mechanism whose end effector platform is linked to the base plate by two independent kinematic chains with a total of five actuators (also referred to as "control mechanisms"). In an embodiment, a first kinematic chain comprises a mobile link and two actuators; and a second kinematic chain comprises a separate mobile link and three actuators. In an embodiment, the number of actuators (two) of the first kinematic chain plus the number of actuators (three) of the second kinematic chain is the same as the number of degrees-of-freedom (five) of the end effector platform. In an embodiment, an alignment guide of the present invention is a five degree-of-freedom parallel manipulator having good positioning accuracy and stability. In an embodiment, this accuracy and stability arises at least in part, from the fact that the legs are working essentially in tension/compression and are subjected to virtually no bending, thereby leading to small unwanted deformations.

Figure 2:
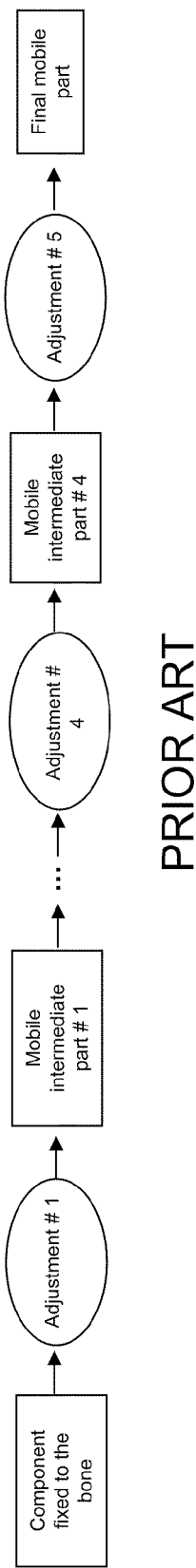
FIG. 2 is a flow chart showing a Prior Art serial manipulator structure having an open loop kinematic chain.

In an embodiment, an alignment guide of the present invention is a parallel kinematic linkage system having a closed kinematic chain, wherein at least two control mechanisms are working in parallel to perform adjustments in two degrees of freedom. In an embodiment, an alignment guide of the present invention is a parallel kinematic linkage system having a closed kinematic chain, wherein at least two control mechanisms are working in parallel to perform adjustments in two degrees of freedom ("a first link"), and wherein at least three control mechanisms are working in parallel to perform adjustments in three additional degrees of freedom ("a second link"), wherein the first link adjustments and the second link adjustments are performed in series. In an embodiment, an alignment guide of the present invention is a parallel kinematic linkage system having a closed kinematic chain as illustrated, for example, in any of schemes 1-29 of FIGS. 1A-1H. FIGS. 1A-1H shows various embodiments of parallel manipulator structures having a closed kinematic chain, wherein at least two control mechanisms are working in parallel to perform adjustments in two degrees of freedom. This is opposed to a serial kinematic linkage system having an open loop kinematic chain meaning that every additional axis is mounted on the previous one, wherein adjustments are performed in series, as illustrated in FIG. 2. An alignment guide of the present invention can have a structure as shown in any of schemes 1-29, wherein at least two control mechanisms are working in parallel to perform adjustments up to, and including, six degrees of freedom. In an embodiment, an alignment guide of the present invention has two control mechanisms working in parallel to perform adjustments in two degrees of freedom (see, for example, schemes 1-3, schemes 5-6, schemes 8-9, schemes 12-15, schemes 19-22, and scheme 24). In an embodiment, an alignment guide of the present invention has three control mechanisms working in parallel to perform adjustments in three degrees of freedom (see, for example, scheme 4, scheme 7, scheme 10, schemes 16-17 and schemes 22-24). In an embodiment, an alignment guide of the present invention has four control mechanisms working in parallel to perform adjustments in four degrees of freedom (see, for example, scheme 11, scheme 18 and scheme 25). In an embodiment, an alignment guide of the present invention has five control mechanisms working in parallel to perform adjustments in five degrees of freedom (see, for example, scheme 26). In an embodiment, an alignment guide of the present invention has six control mechanisms working in parallel to perform adjustments in six degrees of freedom (see, for example, schemes 27-29). An alignment guide of the present invention can have a structure as shown in any of schemes 1-29, as well as additional schemes that may not be present in FIG. 1, wherein at least two control mechanisms are working in parallel to perform adjustments up to, and including, six degrees of freedom.

Detailed embodiments of the present invention are disclosed herein; however, it is to be understood that the disclosed embodiments are merely illustrative of the invention that may be embodied in various forms. In addition, each of the examples given in connection with the various embodiments of the invention is intended to be illustrative, and not restrictive. Further, the figures are not necessarily to scale, some features may be exaggerated to show details of particular components (and any size, material and similar details shown in the figures are, of course, intended to be illustrative and not restrictive). Therefore, specific structural and functional details disclosed herein are not to be interpreted as limiting, but merely as a representative basis for teaching one skilled in the art to variously employ the present invention.

Figure 3:
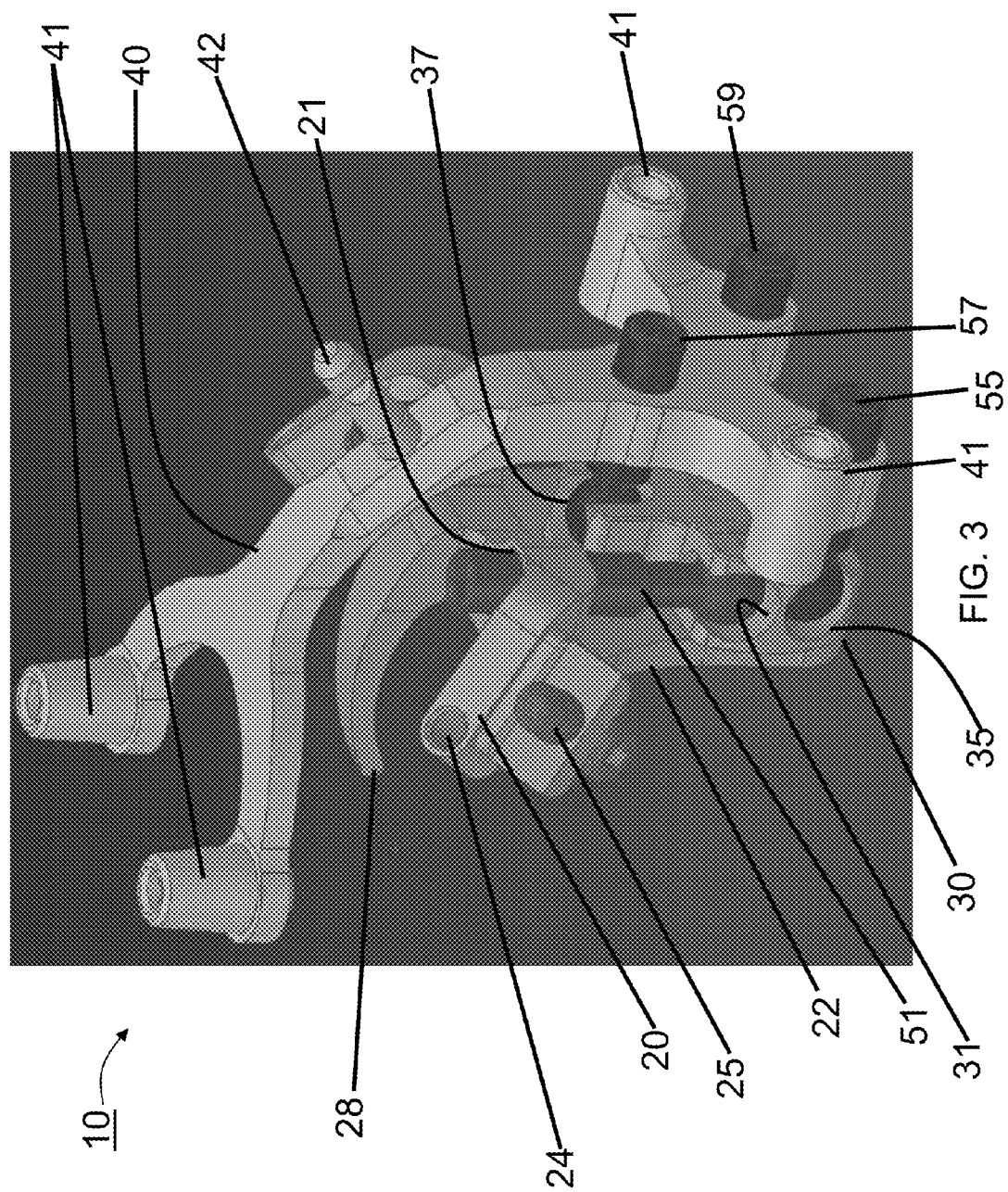
FIG. 3 shows a perspective front view of an embodiment of an alignment guide of the present invention.
Figure 4:
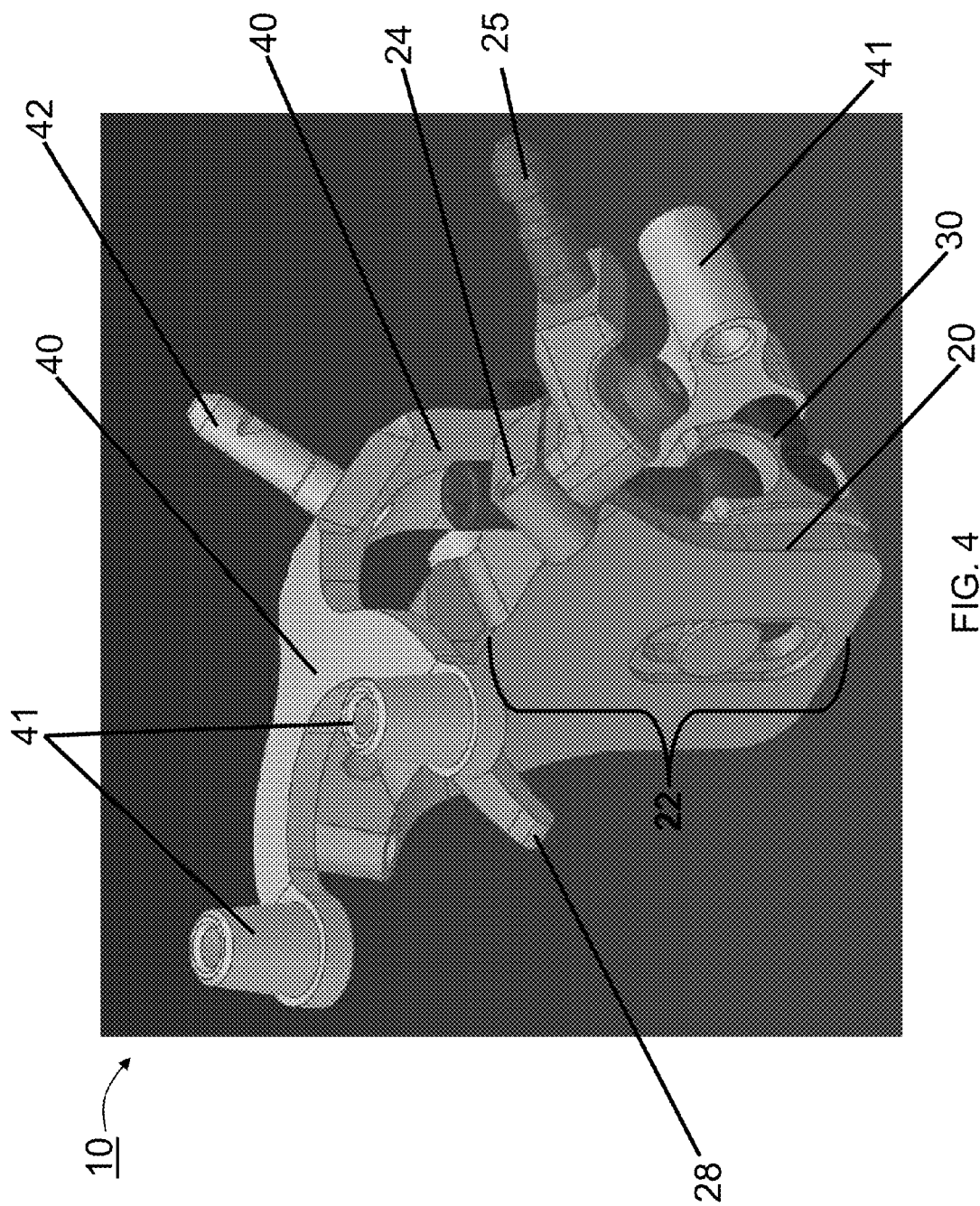
FIG. 4 shows a perspective back view of the alignment guide of FIG. 3.
Figure 5:
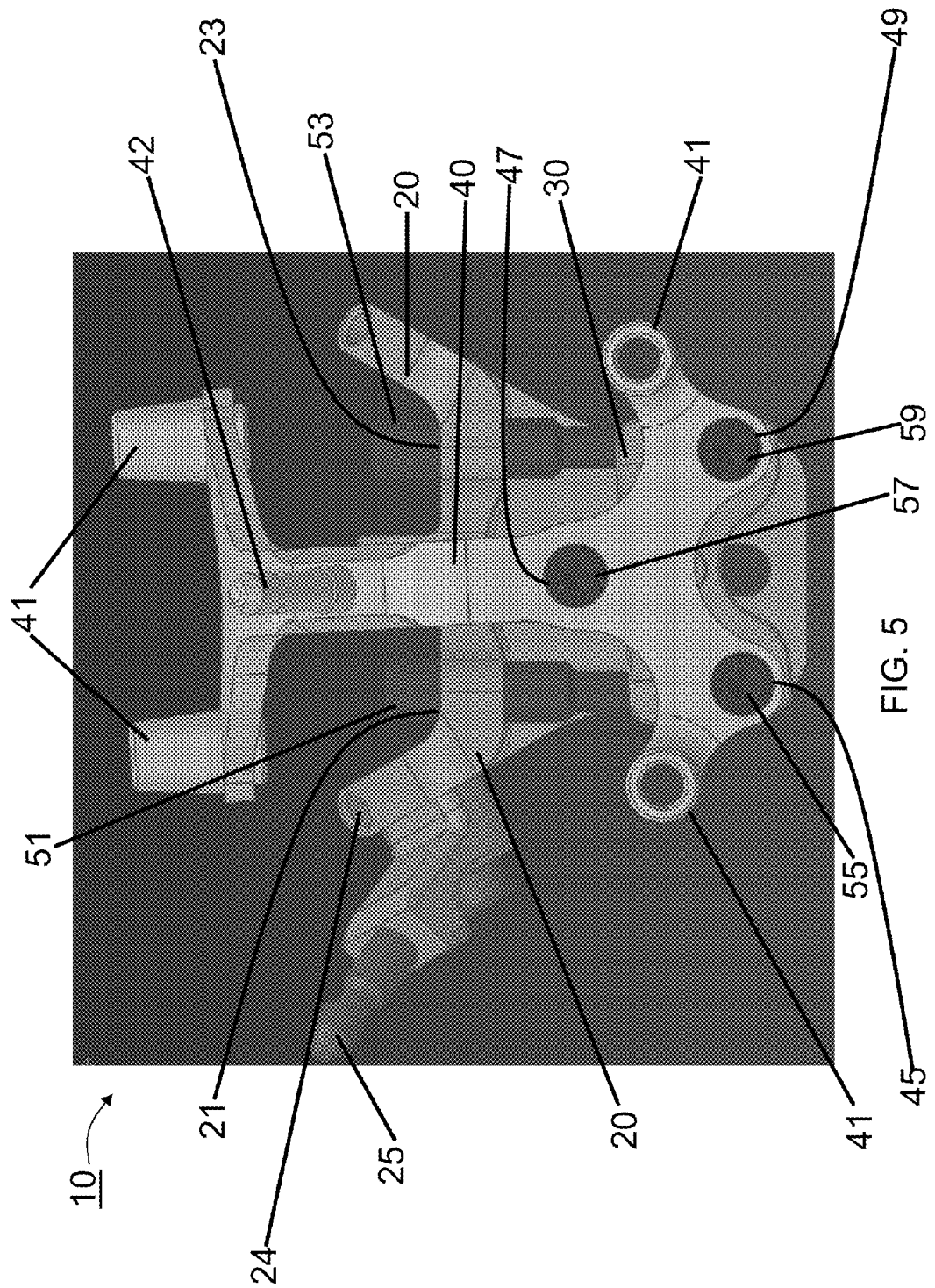
FIG. 5 shows a front view of the alignment guide of FIG. 3.

FIG. 3 in conjunction with FIG. 4 and FIG. 5 shows an embodiment of an alignment guide 10 of the present invention. In an embodiment, the alignment guide 10 is a five degree-of-freedom parallel manipulator made up of a fixed support or base plate 20 connected to an end effector platform 40 with guides 41 by means of a number of "legs". In an embodiment, the alignment guide 10 is a five degree-of-freedom parallel manipulator that is a closed-loop kinematic chain mechanism whose end effector platform 40 is linked to the base plate 20 by two independent kinematic chains (mobile component 30 and actuators 51 and 53; and mobile component 40 and actuators 55, 57 and 59). A closed-loop kinematic chain mechanism is one in which the links and joints are arranged such that at least one closed loop exists. This is opposed to an open loop mechanism such as the serial robot robotic arm (e.g. articulated robots such as jointed arms). In an embodiment, a first kinematic chain comprises mobile link 30 and actuators 51 and 53. In an embodiment, a second kinematic chain comprises mobile link 40 and actuators 55, 57 and 59. In an embodiment, the number of actuators (i.e., two) of the first kinematic chain plus the number of actuators (i.e., three) of the second kinematic chain is the same as the number of degrees-of-freedom (i.e., five) of the end effector platform. In an embodiment, the alignment guide 10 of the present invention is a five degree-of-freedom parallel manipulator having good positioning accuracy. In an embodiment, this accuracy and stability arises at least in part, from the fact that the legs are working essentially in tension/compression and are subjected to virtually no bending, thereby leading to small unwanted deformations.

The alignment guide 10 is used in conjunction with an intraoperative navigation system to prepare a bone element for an implant. The alignment guide 10 includes the first component 20 fixable to a bone element. In an embodiment, the first component 20 is extramedullary fixable to the bone element. The first component 20 includes a first bore 21 that accommodates a first ball head fastener 51, and a second bore 23 that accommodates a second ball head fastener 53. In an embodiment, the first component 20 includes at least one pin hole 24 for accommodating a pin or similar means for removably fixating the first component 20 to the bone element. In an embodiment, the first component 20 serves as a fixed rigid body for surface registration of the femur to create specific anatomic reference points. In an embodiment, the first component 20 serves as a fixed rigid body for surface registration of the femur to create specific anatomic reference points via an active tracking system attached to the first component 20 via attachment 25. In an embodiment, the first component 20 is extramedullary fixable to the bone element via a distal plate 22 of the first component 20. In an embodiment, the first component 20 includes an anterior stylus 28 which can provide guidance for the pre-positioning of the first component 20 relative to the femur, in order to decrease the amount of adjustments (mainly along the antero-posterior axis). The alignment guide 10 also includes the second component 30 moveable with respect to the first component 20. In an embodiment, the second moveable component 30 is rigidly connected to the first component 20. The second component 30 includes a first ball socket 31 that accommodates a first ball of the first ball head fastener 51, a second ball socket (not visible) that accommodates a second ball of the second ball head fastener 53, a third ball socket 35 that accommodates a third ball of a third ball head fastener 55, a fourth ball socket (not visible) that accommodates a fourth ball of a fourth ball head fastener 57, and a fifth ball socket (not visible) that accommodates a fifth ball of a fifth ball head fastener 59. The second component 30, the first ball head fastener 51 and the second ball head fastener 53 form "a first link", wherein two control mechanisms are working in parallel to perform adjustments in two degrees of freedom. The alignment guide 10 also includes the third component 40 moveable with respect to the second component 30 and the first component 20. In an embodiment, the third moveable component 40 is rigidly connected to the second component 30. The third component 40 includes a third bore 45 that accommodates the third ball head fastener 55, a fourth bore 47 that accommodates the fourth ball head fastener 57, and a fifth bore 49 that accommodates the fifth ball head fastener 59. The third component 40, the third ball head fastener 55, the fourth ball head fastener 57 and the fifth ball head fastener 59 form "a second link", wherein three control mechanisms are working in parallel to perform adjustments in up to three additional degrees of freedom. The third component 40 includes the at least one guide 41 for accommodating a surgical instrument for placing at least one hole into the bone element. In an embodiment, the surgical instrument is a drill bit, although other surgical instruments can be used to place holes into the bone element. In the embodiment illustrated in FIGS. 1-3, the third component 40 includes four guides 41. The number of guides 41 can vary for a particular application of the alignment guide 10. One, two, three, four, five, six or more guides 41 may be included. In an embodiment, the third component 40 serves as a mobile body to produce a moving digital image of patient's femur as it is moved during the operation via an active tracking system attached to the third component 40 via attachment 42.

The first ball head fastener 51 and the second ball head fastener 53 are working in parallel to perform adjustments in two degrees of freedom so as to result in two degrees of freedom alignment of the guides 41 for preparing the bone element for the implant, and the third ball head fastener 55, the fourth ball head fastener 57 and the fifth ball head fastener 59 are working in parallel to perform adjustments in up to three additional degrees of freedom so as to result in up to three additional degrees of freedom alignment of the guides 41 for preparing the bone element for the implant. In an embodiment, adjustments are made to control up to six degrees of freedom selected from the group consisting of flexion/extension angle, varus/valgus angle, distal cut resection level, anterior/posterior positioning, internal/external rotation and medio/lateral positioning. It should be noted that the actuators (i.e., control mechanisms) of a kinematic chain of the parallel manipulator alignment guide 10 are not limited to a ball/socket type as described herein. Other actuators/control mechanisms can be used including, but not limited to, gliding type, hinge type, saddle type and pivot type. In an embodiment, the actuator is a rack and pinion linear actuator that comprises a pair of gears, and a ratchet device is used to lock travel of the pinion on the rack. In an embodiment, the actuator is a cam linear actuator having an indicating device (e.g., a dial) such that the intraoperative navigation system can inform the surgeon what position to turn the cam to, eliminating the need to refer to the display screen of the system when adjusting the cam actuator.

Figure 6:
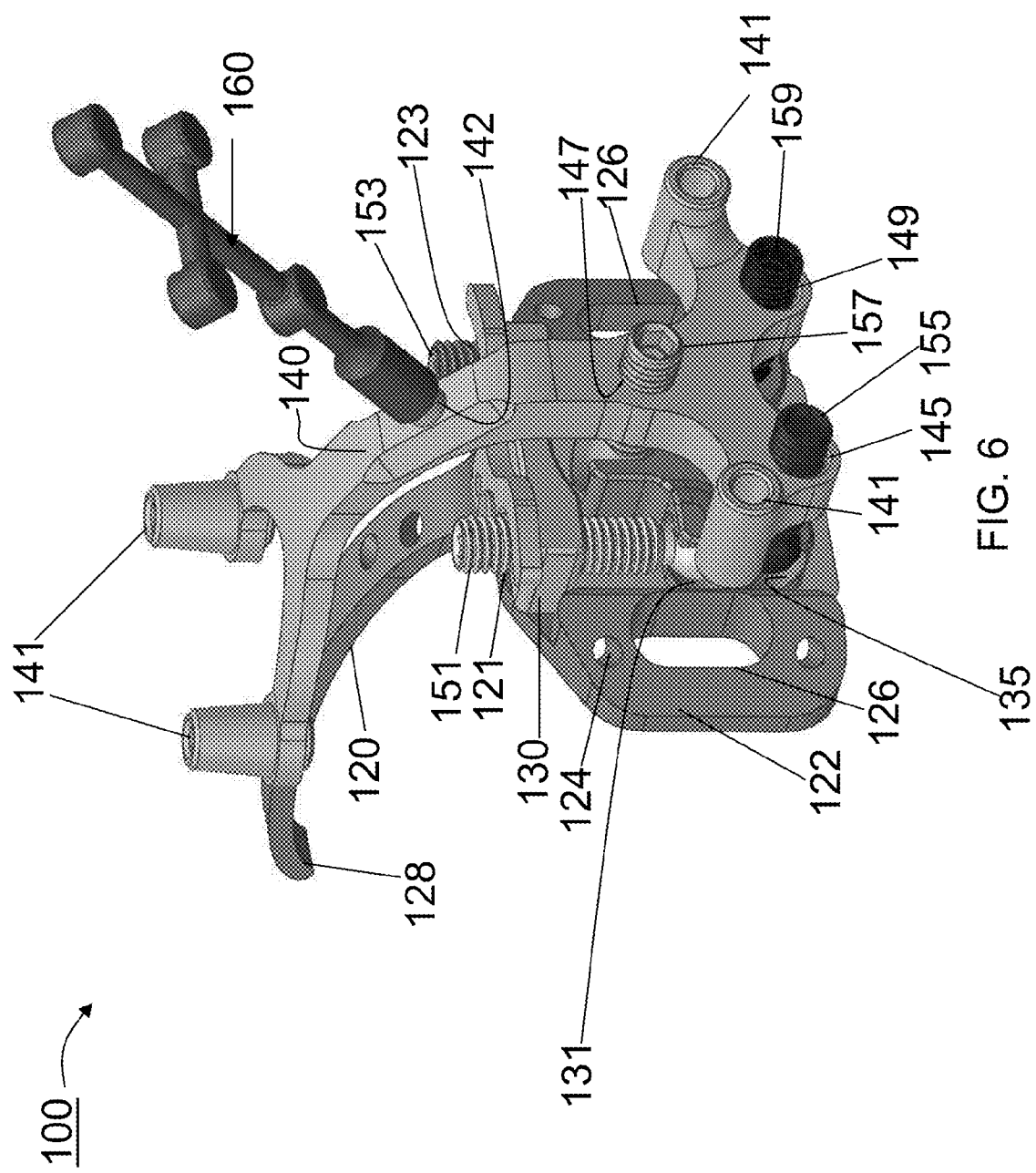
FIG. 6 shows a perspective front view of an embodiment of an alignment guide of the present invention.

FIG. 6 shows an embodiment of an alignment guide 100 of the present invention. In an embodiment, the alignment guide 100 is a five degree-of-freedom parallel manipulator made up of a fixed support or base plate 120 connected to an end effector platform 140, where guides 141 are attached, by means of a number of "legs". In an embodiment, the alignment guide 100 is a five degree-of-freedom parallel manipulator that is a closed-loop kinematic chain mechanism whose end effector platform 140 is linked to the base plate 120 by two independent kinematic chains (mobile component 130 and actuators 351 and 353; and mobile component 140 and actuators 155, 157 and 159). A closed-loop kinematic chain mechanism is one in which the links and joints are arranged such that at least one closed loop exists. This is opposed to an open loop mechanism such as the serial robot robotic arm (e.g. articulated robots such as jointed arms). In an embodiment, a first kinematic chain comprises mobile link 130 and actuators 151 and 153. In an embodiment, a second kinematic chain comprises mobile link 140 and actuators 155, 157 and 159. In an embodiment, the number of actuators (two) of the first kinematic chain plus the number of actuators (three) of the second kinematic chain is the same as the number of degrees-of-freedom (five) of the end effector platform. In an embodiment, the alignment guide 100 of the present invention is a five degree-of-freedom parallel manipulator having good positioning accuracy. This accuracy and stability arises at least in part, from the fact that the legs are working essentially in tension/compression and are subjected to virtually no bending, thereby leading to small unplanned deformations.

The alignment guide 100 is used in conjunction with an intraoperative navigation system to prepare a bone element for an implant. The alignment guide 100 includes the first component 120 fixable to a bone element. In an embodiment, the first component 120 is extramedullary fixable to the bone element. In an embodiment, the first component 120 serves as a fixed rigid body. In an embodiment, the first component 120 includes at least one pin hole 124 for accommodating a pin or similar means for removably fixating the first component 120 to the bone element. In an embodiment, the first component 120 is extramedullary fixable to the bone element via a distal plate 122. In an embodiment, the first component 120 includes and an anterior stylus 128 which can act as a guide to register, for example, the anterior femoral cortex of a femur. The alignment guide 100 also includes the second component 130 moveable with respect to the first component 120. In an embodiment, the second moveable component 130 is rigidly connected to the first component 120. The second component 130 includes a first bore 121 that accommodates a first ball head fastener 151, and a second bore 123 that accommodates a second ball head fastener 153. The second component 130 also includes a first ball socket 131 that accommodates a first ball of the first ball head fastener 151, a second ball socket (not visible) that accommodates a second ball of the second ball head fastener 153, a third ball socket 135 that accommodates a third ball of a third ball head fastener 155, a fourth ball socket (not visible) that accommodates a fourth ball of a fourth ball head fastener 157, and a fifth ball socket (not visible) that accommodates a fifth ball of a fifth ball head fastener 159. The second component 130, the first ball head fastener 151 and the second ball head fastener 153 form "a first link", wherein two control mechanisms are working in parallel to perform adjustments in two degrees of freedom. The alignment guide 100 also includes the third component 140 moveable with respect to the second component 130 and the first component 120. In an embodiment, the third moveable component 140 is rigidly connected to the second component 130. The third component 140 includes a third bore 145 that accommodates the third ball head fastener 155, a fourth bore 147 that accommodates the fourth ball head fastener 157, and a fifth bore 149 that accommodates the fifth ball head fastener 159. The third component 140, the third ball head fastener 155, the fourth ball head fastener 157 and the fifth ball head fastener 159 form "a second link", wherein three control mechanisms are working in parallel to perform adjustments in up to three additional degrees of freedom. The third component 140 includes at least one guide 141 for accommodating a surgical instrument for placing at least one hole into the bone element. In an embodiment, the surgical instrument is a drill bit, although other surgical instruments can be used to place holes into the bone element. In the embodiment illustrated in FIG. 6, the third component 140 includes four guides 141. The number of guides 141 can vary for a particular application of the alignment guide 100. One, two, three, four, five, six or more guides 141 may be included. As illustrated in the embodiment of FIG. 6, the distal plate 122 of the first component 120 includes two cut-outs 126, wherein each of the two cut-outs 126 line up with each of the lower guides 141 of the third component 140 to accommodate the surgical instrument for placing holes into the bone element. In an embodiment, the third component 140 serves as a mobile body to produce a moving digital image of patient's femur as it is moved during the operation via an active tracking system 160 attached to the third component 140 via attachment 142.

The first ball head fastener 151 and the second ball head fastener 153 are arranged in parallel to perform adjustment in two degrees of freedom so as to result in two degrees of freedom alignment of the guides 141 for preparing the bone element for the implant, and the third ball head fastener 155, the fourth ball head fastener 157 and the fifth ball head fastener 159 are arranged in parallel to perform adjustments of up to three additional degrees of freedom so as to result in up to three additional degrees of freedom alignment of the guides 141 for preparing the bone element for the implant. In an embodiment, adjustments are made to control up to five degrees of freedom selected from the group consisting of flexion/extension angle, varus/valgus angle, distal cut resection level, anterior/posterior positioning, internal/external rotation and medio/lateral positioning. It should be noted that the actuators (i.e., control mechanisms) of a kinematic chain of the parallel manipulator alignment guide 100 are not limited to a ball/socket type as described herein. Other actuators/control mechanisms can be used including, but not limited to, gliding type, hinge type, saddle type and pivot type. In an embodiment, the actuator is a rack and pinion linear actuator that comprises a pair of gears, and a ratchet device is used to lock travel of the pinion on the rack. In an embodiment, the actuator is a cam linear actuator having an indicating device (e.g., a dial) such that the intraoperative navigation system can inform the surgeon what position to turn the cam to, eliminating the need to refer to the display screen of the system when adjusting the cam actuator.

Figure 7B:
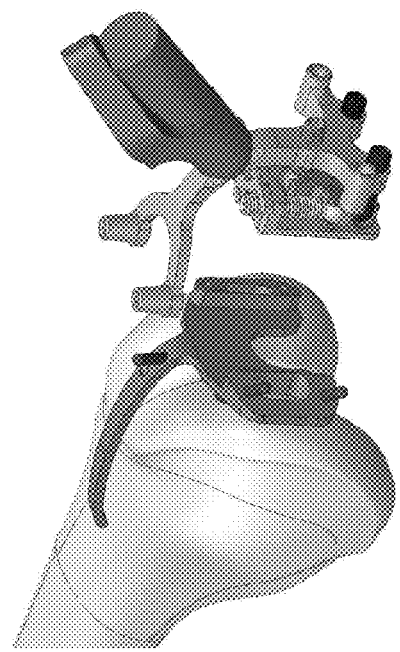
FIGS. 7A and 7B show perspective front views of the alignment guide of FIG. 6 fixed to a bone element for preparing the bone element for an implant.
Figure 7A:
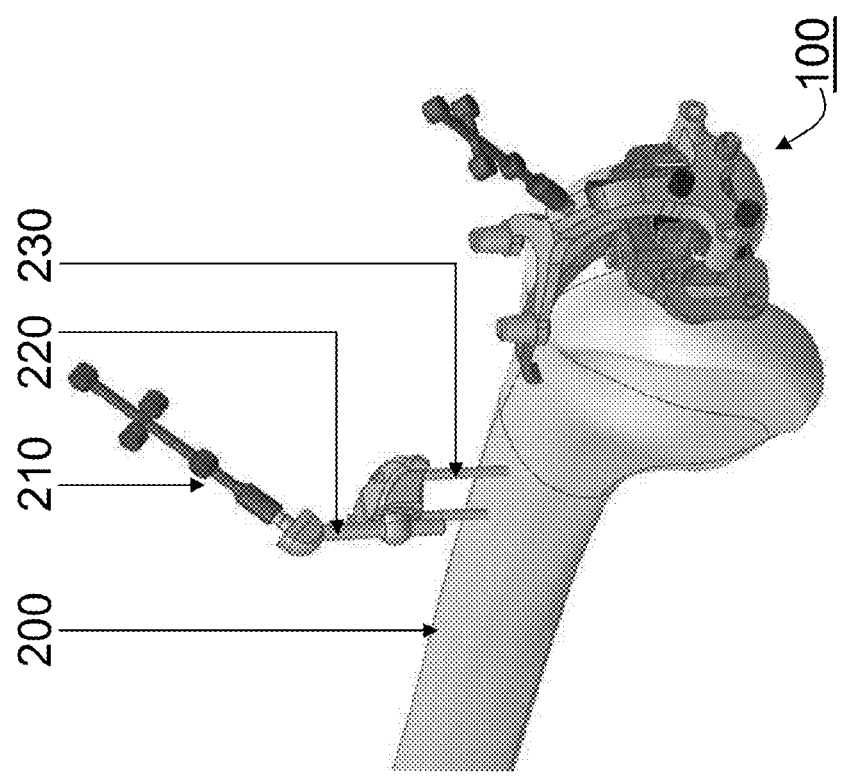

FIGS. 7A and 7B details an embodiment of implementation of a tracker system with the alignment guide 100 of FIG. 6. As illustrated in FIG. 7B, the alignment guide 100 may be made modular such that the second component 130 and the third component 140 are removable from the first component 120. Similarly, the alignment guide 100 may be made modular such that the third component 140 is removable from the second component 130, and the second component 130 is removable from the first component 120. In an embodiment, a surgeon reconstructs the patient's bone 200 (e.g., the femur)

as a solid body using a CAOS system. In order to establish this virtual bone based on the characterization of boney landmarks, an established referential created by a so-called fixed tracker 210 linked to a solid body is used. In an embodiment, the fixed tracker 210 can be attached to the diaphyseal part of the femur 200 using a support 220 directly attached to the bone 200 using a set of conventional locking pins 230 while the mobile tracker 160 is attached to the third component 40 of the alignment guide 100. In other embodiments of the present invention, the fixed tracker can be directly attached to a first component of an alignment guide of the present invention. After the bone is characterized as a solid body relative to its attached referential, the surgeon defines the optimum implant size and implant placement using the CAOS system. These parameters defined, the surgeon reproduces them by adjusting the orientation of the second component 130 relative to the first component 120, and the third component 140 relative to the second component 130 and the first component 120. In order to allow the CAOS system to monitor the orientation of the mobile components 130 and 140 relative to the fixed tracker 210, the mobile tracker 160 is attached to the third component 140. Reproducing the optimum parameters is obtained by adjusting the orientation and location of the second component 130 and the third component 140 relative to the first component 120 using adjustment mechanisms 151, 153, 155, 157 and 159. The CAOS system can figure out how many adjustments need to be made to each adjustment mechanism 151, 153, 155, 157 and 159 and can continuously monitor the surgeons adjustments to intraoperatively monitor the procedure.

Figure 8A:
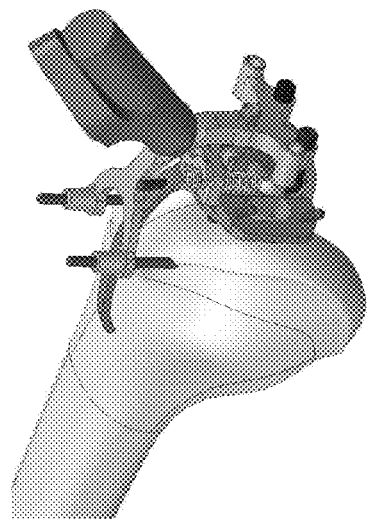
FIGS. 8A-8I show perspective views of an embodiment of a method of preparing a femur for receiving an implant using the alignment guide of FIG. 6.

FIGS. 8A-8I show perspective views of an embodiment of a method of preparing a femur for receiving an implant using the alignment guide 100. Similar methods can be performed using alignment guide 10 of the present invention. As illustrated in FIG. 8A, a surgeon links a fixed tracker (not represented) with the femur 200 and characterizes the bone in the attached referential using any known technique. Based on this information, the surgeon will define the optimum size, location, and orientation for the femoral component of the implant to be implanted using the CAOS system. The surgeon places the alignment guide 100 in position against the femur 200. In an embodiment, the surgeon can reference the anterior femoral cortex and the distal condyles by the anterior stylus 128 and the distal plate 122, respectively. Such constraint allows placement of the alignment guide 100 in an anatomical and repeatable position relative to the femur 200. This placement done, the surgeon securely fixes the first component 120 of the alignment guide 100 to the bone 200 using, for example, conventional locking pins.

Figure 8B:
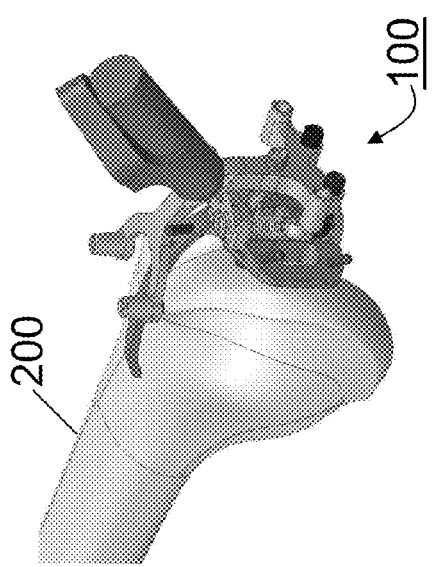
Figure 8C:
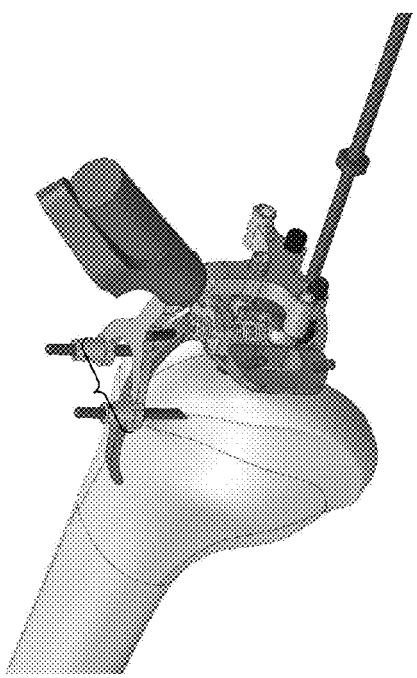
Figure 8D:
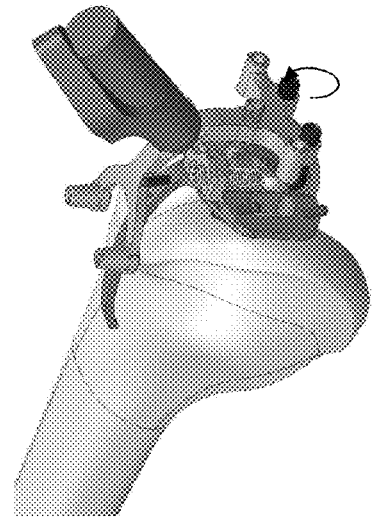
Figure 8G:
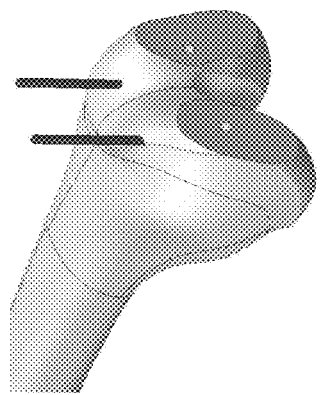
Figure 8H:
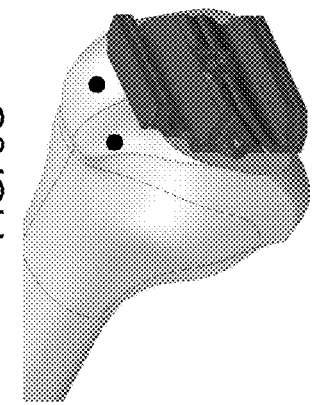
Figure 8I:
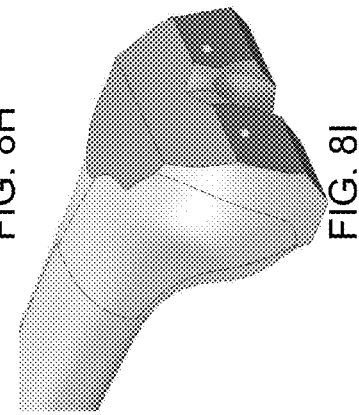
Figure 8E:
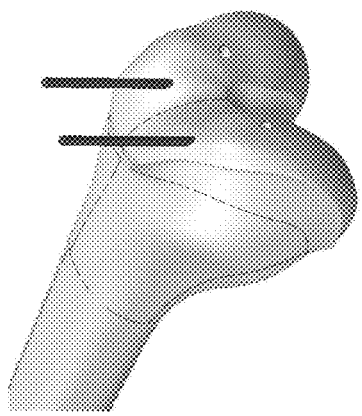
Figure 8F:
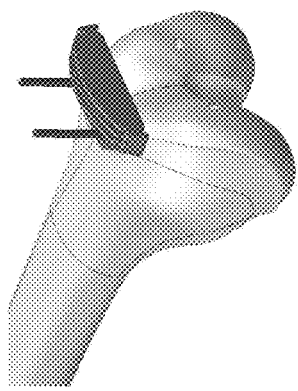

As illustrated in FIG. 8B, with the first component 120 of the alignment guide 100 secured to the bone 200, the surgeon adjusts the mobile components 130 and 140 relative to the first component 120, in order to reproduce the optimum size, location and orientation of the femoral component defined using the CAOS. The adjustment is performed using the set of adjustment components mechanisms 151, 153, 155, 157 and 159. As illustrated in FIG. 8C, with the adjustment established, the surgeon drills two holes on the anterior femoral cortex through the upper guides 141, and preferably leaves the drill bits attached to the bone 200 through the two holes. The adjustments made to the alignment guide 100 in conjunction with the navigation results in improved accuracy of drilling of the holes. As illustrated in FIG. 8D, two holes are drilled on the distal condyles through the lower guides 141 using a drill bit. As illustrated in FIG. 8E, the alignment guide 100 is removed from the femur 200. The two sets of two holes duplicate the location and orientation of the femoral component to be implanted. As illustrated in FIG. 8F, a conventional distal cutting block is positioned on the two anterior pins implanted on the two anterior holes, and a femoral distal cut is performed. As illustrated in FIG. 8G, the conventional distal cutting block is removed from the femur 200. As illustrated in FIG. 8H, a conventional 4-in-1 cutting block is positioned relative to the femur 200 using the set of two holes present on the distal femur, and femur preparation is completed. FIG. 8I shows the femur 200 completely prepared. It should be understood that other types of cutting blocks could be used to prepare the femur and are within the scope and spirit of the present invention.

Figure 9:
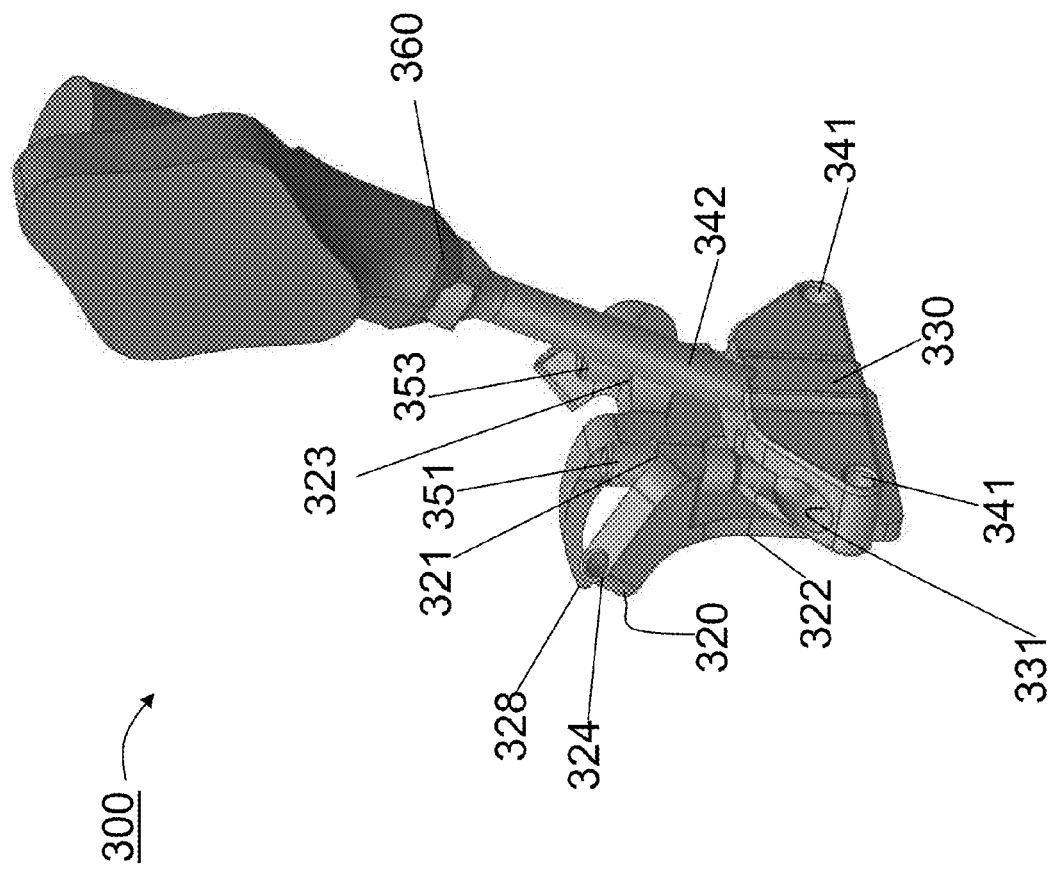
FIG. 9 shows a perspective view of an embodiment of an alignment guide of the present invention.

FIG. 9 shows a perspective view of an embodiment of an alignment guide 300 of the present invention. In the embodiment illustrated in FIG. 9, the alignment guide 300 is a two degree-of-freedom parallel manipulator with only one parallel chain of adjustment, as compared to the alignment guide 10 and the alignment guide 100 which are parallel manipulators having a series of parallel chains. In an embodiment, the alignment guide 300 is a two degree-of-freedom parallel manipulator made up of a fixed support or base plate 320 connected to an end effector platform 340 with guides 341 by means of a number of "legs". In an embodiment, the alignment guide 300 is a two degree-of-freedom parallel manipulator that is a closed-loop kinematic chain mechanism whose end effector platform 340 is linked to the base plate 320 by one independent kinematic chain (mobile component 330 and actuators 351 and 353). A closed-loop kinematic chain mechanism is one in which the links and joints are arranged such that at least one closed loop exists. This is opposed to an open loop mechanism such as the serial robot robotic arm (e.g. articulated robots such as jointed arms). In an embodiment, kinematic chain comprises mobile link 330 and actuators 351 and 353. In an embodiment, the number of actuators (i.e., two) of the kinematic chain is the same as the number of degrees-of-freedom (i.e., two) of the end effector platform. In an embodiment, the alignment guide 300 of the present invention is a two degree-of-freedom parallel manipulator having good positioning accuracy. In an embodiment, this accuracy and stability arises at least in part, from the fact that the legs are working essentially in tension/compression and are subjected to virtually no bending, thereby leading to small unwanted deformations.

The alignment guide 300 is used in conjunction with an intraoperative navigation system to prepare a bone element for an implant. The alignment guide 300 includes the first component 320 fixable to a bone element. In an embodiment, the first component 320 is extramedullary fixable to the bone element. In an embodiment, the first component 320 serves as a fixed rigid body. The first component 320 includes a first bore 321 that accommodates a first ball head fastener 321, and a second bore 323 that accommodates a second ball head fastener 353. In an embodiment, the first component 320 includes at least one pin hole 324 for accommodating a pin or similar means for removably fixating the first component 320 to the bone element. In an embodiment, the first component 320 is extramedullary fixable to the bone element via a distal plate 322. In an embodiment, the first component 320 includes and an anterior stylus 328 which can act as a guide to register, for example, the anterior femoral cortex of a femur. The alignment guide 300 also includes the second component 330 moveable with respect to the first component 320. In an embodiment, the second moveable component 330 is rigidly connected to the first component 320. The second component 330 includes a first ball socket 331 that accommodates a first ball of the first ball head fastener 351 and a second ball socket (not visible) that accommodates a second ball of the second ball head fastener 353. The first ball head fastener 351 and the second ball head fastener 353 are arranged in parallel to perform adjustments in two degrees of freedom. The second component 330 includes the at least one guide 341 for accommodating a surgical instrument for placing holes into the bone element. In an embodiment, the surgical instrument is a drill bit, although other surgical instruments can be used to place holes into the bone element. In the embodiment illustrated in FIG. 9, the second component 330 includes four guides 341. The number of guides 341 can vary for a particular application of the alignment guide 300. One, two, three, four, five, six or more guides 341 may be included. In an embodiment, the second component 330 serves as a mobile body to produce a moving digital image of patient's femur as it is moved during the operation via an active tracking system 360 attached to the second component 330 via attachment 342.

The first ball head fastener 351 and the second ball head fastener 353 are arranged in parallel to perform adjustment of two degrees of freedom so as to result in two degrees of freedom alignment of the guides 341 for preparing the bone element for the implant. In an embodiment, adjustments are made to control up to two degrees of freedom selected from the group consisting of flexion/extension angle, varus/valgus angle, distal cut resection level, anterior/posterior positioning and internal/external rotation. It should be noted that the actuators (i.e., control mechanisms) of a kinematic chain of the parallel manipulator alignment guide 300 are not limited to a ball/socket type as described herein. Other actuators/control mechanisms can be used including, but not limited to, gliding type, hinge type, saddle type and pivot type. In an embodiment, the actuator is a rack and pinion linear actuator that comprises a pair of gears, and a ratchet device is used to lock travel of the pinion on the rack. In an embodiment, the actuator is a cam linear actuator having an indicating device (e.g., a dial) such that the intraoperative navigation system can inform the surgeon what position to turn the cam to, eliminating the need to refer to the display screen of the system when adjusting the cam actuator.

In an embodiment, an alignment guide for preparing a bone element for receiving an implant includes a first component fixable to the bone element, wherein the first component serves as a fixed rigid body; a second component moveable with respect to the first component; and a third component moveable with respect to the second component and the first component, the third component comprising at least one guide that accommodates a surgical instrument, wherein the second component and n control mechanisms form a first link, wherein n control mechanisms are working in parallel to perform adjustments in up to n degrees of freedom of the alignment guide so as to result in up to n degrees of freedom alignment of the at least one guide for preparing the bone element for the implant, wherein the third component and m control mechanisms form a second link, wherein m control mechanisms are working in parallel to perform adjustments in up to m additional degrees of freedom of the alignment guide so as to result in up to m additional degrees of freedom alignment of the at least one guide for preparing the bone element for the implant, and wherein a total degree of freedom adjustment of the at least one guide relative to the first component is up to n+m degrees of freedom. In an embodiment, n is at least two and m is at least two. In an embodiment, n is two and m is two. In an embodiment, n is two and m is three. In an embodiment, n is two and m is four. In an embodiment, n is two and m is five. In an embodiment, n is at least three. In an embodiment, n is three and m is two. In an embodiment, n is three and m is three. In an embodiment, n is at least four. In an embodiment, n is four and m is two.

In an embodiment, an alignment guide for preparing a bone element for receiving an implant includes a first component fixable to the bone element, wherein the first component serves as a fixed rigid body; a second component moveable with respect to the first component; a third component moveable with respect to the second component and the first component; and a fourth component moveable with respect to the third component, the second component, and the first component, the fourth component comprising at least one guide that accommodates a surgical instrument, wherein the second component and n control mechanisms form a first link, wherein n control mechanisms are working in parallel to perform adjustments in up to n degrees of freedom of the alignment guide so as to result in up to n degrees of freedom alignment of the at least one guide for preparing the bone element for the implant, wherein the third component and m control mechanisms form a second link, wherein m control mechanisms are working in parallel to perform adjustments in up to m additional degrees of freedom of the alignment guide so as to result in up to m additional degrees of freedom alignment of the at least one guide for preparing the bone element for the implant, wherein the fourth component and o control mechanisms form a third link, wherein o control mechanisms are working in parallel to perform adjustments in up to o degrees of freedom of the alignment guide so as to result in up to o degrees of freedom alignment of the at least one guide for preparing the bone element for the implant, and wherein a total degree of freedom adjustment of the at least one guide relative to the first component is up to n+m+o degrees of freedom. In an embodiment, n is two, m is two, and o is two.

An alignment guide of the present invention includes at least one guide that accommodates a surgical instrument. In an embodiment, the at least one guide helps position the surgical instrument at a precise position on the bone element. In an embodiment, the at least one guide helps position the surgical instrument at a precise position on the bone element to create at least one hole in the bone element. In an embodiment, the at least one guide of the alignment guide is part of the final mobile component. In such embodiments, a total degree of freedom adjustment of the at least one guide relative to the first fixed component can be the sum of the degree of freedom adjustment in each mobile component. In an embodiment, an alignment guide having a first fixed component, a second mobile component with two control mechanisms, and a third mobile component with three control mechanisms, wherein the third component includes at least one guide for accommodating a surgical instrument, can have a total of up to five degree of freedom adjustment of the at least one guide relative to the first fixed component. In an embodiment, an alignment guide having a first fixed component, a second mobile component with three control mechanisms, and a third mobile component with three control mechanisms, wherein the third component includes at least one guide for accommodating a surgical instrument, can have a total of up to six degree of freedom adjustment of the at least one guide relative to the first fixed component. In an embodiment, the at least one guide of the alignment guide is part of an intermediate mobile component. In an embodiment, at least one guide of the alignment guide is part of an intermediate mobile component, and at least one additional guide of the alignment guide is part of a final mobile component.

In an embodiment, the methodology of the present invention is based on the use of an intraoperative navigation system and of a reduced and compact alignment guide for alignment of implant components during replacement surgery. In an embodiment, the intraoperative navigation system incorporates a computer digitizer to track the location of the patient and an alignment guide in space. Different digitizer modalities are within the scope and spirit of the present invention, including, but not limited to, optical, electromagnetic, electromechanical, and ultrasonographic. In an embodiment, the digitizer modality used with the present invention is an optical tracking system. Optically based systems within the scope and spirit of the present invention include active and passive tracking systems. Active tracking systems use infrared, light-emitting diodes attached to the patient and to an alignment guide of the present invention. Passive tracking system use reflective spheres (instead of diodes) to reflect infrared light from an infrared emitter back to a receiver. Both the emitter and receiver are located in 1 digitzer camera. A registration process may be necessary to accurately define the location of the patient for the CAOS system. Registration may be accomplished by identification of specific fiducial markers (i.e., stable landmarks that can be identified on both the virtual and real patients) on the virtual patient as seen on the navigation system monitor. In an embodiment, a first component of an alignment guide of the present invention is coupled with a sensing device. In an embodiment, the fixed sensing device can be used to register the femur to a preoperative plan. In an embodiment, a second component and/or a third component of an alignment guide of the present invention is coupled with a second sensing device. In an embodiment, the second sensing device can be used for tracking orientation and relative displacement of the mobile components of the alignment guide relative to the fixed first component.

In an embodiment, a method for preparing a bone element for receiving an implant includes fixing a first component of an alignment guide of the present invention in place against a femur using standard pins implanted through the bore of the first component. From this point, a surgeon can register anatomical landmarks such as posterior femoral condyles, distal femoral condyles, anterior cortex of the femur, and epicondylar axis in order to define the optimum orientation and location of a femoral component of an implant. Registering the anatomical landmarks can be accomplished using, for example, at least one fixed navigation tracker of a CAOS system. In an embodiment, one of the fixed navigation trackers can be attached to the first component of the alignment guide. In order to reproduce the optimum orientation and location of the implant on the patient's femur, adjustments to a second component and a third component of the alignment guide are made using control mechanisms of the alignment guide to properly position at least one guide of the alignment guide in a proper position for preparing the bone element for the implant. Adjustments to the second component and the third component can be tracked using a mobile navigation tracker attached to the second component, the third component or both components. In an embodiment, the alignment guide includes five control mechanisms for adjusting up to five degrees of freedom. In an embodiment, the control mechanisms are five color-coded adjustment fasteners, such as ball head screws. The ball head fasteners can be adjusted according to the number of turns as well as direction (i.e., clockwise or counterclockwise) defined by the CAOS system for each preferably color-coded fastener. In an embodiment, the adjustment of the fasteners is performed manually, for example using a screwdriver or any type of instrument allowing the rotation of a screw. In an embodiment, the adjustment of the fasteners is performed robotically, for example using a robotic arm of the CAOS system. The adjustment performed, holes can be positioned in the bone element by drill bits or other similar means positioned through the guides. The holes obtained through the lower guides define the location and orientation of the femoral distal cut, while holes obtained through the upper guides define the location and orientation of the 4-in-1 cutting block relative to the distal femoral cut.

In an embodiment, a method of preparing a femur for receiving an implant includes fixing, a first component of an alignment guide to distal condyles of the femur; tracking orientation and relative displacement of a second component of the alignment guide with respect to the first component using a mobile navigation tracker; controlling up to n degrees of freedom of the alignment guide by parallel adjustment of the second component relative to the first component to position the second component in a desired position relative to the femur; tracking orientation and relative displacement of a third component of the alignment guide with respect to the second component and the first component using the mobile navigation tracker; controlling up to m additional degrees of freedom of the alignment guide by parallel adjustment of the third component relative to the second component and the first component to position the third component in a desired position relative to the femur; forming at least one hole on a femoral cortex of the femur using a drill bit or similar means; maintaining the drill bit on the femoral cortex so as to serve as a fixation means; forming at least one hole on the distal condyles of the femur; removing the alignment guide from the femur; positioning a cutting block attachable to the fixation means on the femoral cortex; performing a distal femoral resection using the cutting block as a guide; removing the cutting block from the anterior femoral cortex; positioning a cutting block on the distal condyles based on the hole formed on the distal condyles; and completing resection of the femur for receiving the implant.

In an embodiment, the methodology of the present invention is based on the use of CAOS and of a reduced and compact alignment guide for alignment of knee implant components because of the precision the surgeon may get with femoral and tibial bone cuts. In an embodiment, the methodology of the present invention is based on the use of CAOS and of a reduced and compact alignment guide for alignment of acetabular implant components to navigate acetabular component placement where correct cup inclination is crucial. In an embodiment, the methodology of the present invention is based on the use of CAOS and of a reduced and compact alignment guide for alignment of shoulder implant components, where CAOS provides guidance for the preparation of the glenoid and the humerus as well as spine indication.

An alignment guide of the present invention can be made from materials known as being biocompatible and used for surgical instrumentation, including, but not limited to, steel alloys (e.g., stainless steel), polymers (e.g., polyphenylsulfone and polyetherimide), titanium and titanium alloys and combinations thereof. An alignment guide of the present invention can be made to be single-use, and discarded after a surgical operation. An alignment guide of the present invention can have adjustment components that are color-coded to guide a surgeon while reproducing the CAOS-determined optimal cutting plateaus (e.g., the instrument turns the yellow screw clockwise six times, turns the green screw counterclockwise twice, etc.). An alignment guide of the present invention can be manufactured to include one or more cutting slots intended to receive, for example, a sawblade to cut the bone element instead of a guide, or can feature a combination cutting slot and guide. For example, a cutting slot can be used to perform the distal femoral cut, while a guide can be used to drill two holes to define the position of the 4-in-1 cutting block.

While a number of embodiments of the present invention have been described, it is understood that these embodiments are illustrative only, and not restrictive, and that many modifications may become apparent to those of ordinary skill in the art. For example, any element described herein may be provided in any desired size (e.g., any element described herein may be provided in any desired custom size or any element described herein may be provided in any desired size selected from a "family" of sizes, such as small, medium, large). Further, one or more of the components may be made from any of the following materials: (a) any biocompatible material (which biocompatible material may be treated to permit surface bone ingrowth or prohibit surface bone ingrowth—depending upon the desire of the surgeon); (b) a metal such as a pure metal including, but not limited to, titanium and/or an alloy such as Ti—Al—Nb, Ti-6Al-4V and/or stainless steel; (c) a polymer, or any combination thereof. Further still, any metal construct may be a machined metal construct. Further still, any steps described herein may be carried out in any desired order (and any additional steps may be added as desired and/or any steps may be deleted as desired).

It will be appreciated that several of the above-disclosed and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

What is claimed is:

1. An alignment guide for preparing a bone element for receiving an implant comprising:
a first component fixable to the bone element comprising:
a first bore that accommodates a first ball head fastener; and
a second bore that accommodates a second ball head fastener,
wherein the first component serves as a fixed rigid body;
a second component moveable with respect to the first component comprising:
a first ball socket that accommodates a first ball of the first ball head fastener;
a second ball socket that accommodates a second ball of the second ball head fastener; and
a third ball socket that accommodates a third ball of a third ball head fastener; and
a third component moveable with respect to the second component and the first component, the third component comprising:
a third bore that accommodates the third ball head fastener; and
at least one guide that accommodates a surgical instrument,
wherein the first ball head fastener and the second ball head fastener are working in parallel to perform adjustments in up to two degrees of freedom so as to result in up to two degrees of freedom alignment of the at least one guide for preparing the bone element for the implant, and wherein the third ball head fastener adjusts a third additional degree of freedom so as to result in three degrees of freedom alignment of the at least one guide for preparing the bone element for the implant.

2. The alignment guide of claim 1 wherein the first component includes at least one bore for accommodating a fastener for removably fixating the first component to the bone element.

3. The alignment guide of claim 1 wherein adjustments are made to control up to two degrees of freedom selected from the group consisting of flexion/extension angle, varus/valgus angle, distal cut resection level, anterior/posterior positioning, internal/external rotation and medio/lateral positioning.

4. The alignment guide of claim 1 wherein the first component further comprises a navigation tracker of a computer-assisted navigation system.

5. The alignment guide of claim 1 wherein the second component further comprises a navigation tracker of a computer-assisted navigation system.

6. The alignment guide of claim 1 wherein orientation and relative displacement of the second component relative to the first component is continuously adjustable to control the two degrees of freedom.

7. An alignment guide for preparing a bone element for receiving an implant comprising:
a first component fixable to the bone element comprising:
a first bore that accommodates a first ball head fastener; and
a second bore that accommodates a second ball head fastener,
wherein the first component serves as a fixed rigid body;
a second component moveable with respect to the first component comprising:
a first ball socket that accommodates a first ball of the first ball head fastener;
a second ball socket that accommodates a second ball of the second ball head fastener;
a third ball socket that accommodates a third ball of a third ball head fastener;
a fourth ball socket that accommodates a fourth ball of a fourth ball head fastener; and
a fifth ball socket that accommodates a fifth ball of a fifth ball head fastener; and
a third component moveable with respect to the second component and the first component comprising:
a third bore that accommodates the third ball head fastener;
a fourth bore that accommodates the fourth ball head fastener;
a fifth bore that accommodates the fifth ball head fastener; and
at least one guide that accommodates a surgical instrument,
wherein the first ball head fastener and the second ball head fastener are working in parallel to perform adjustments in up to two degrees of freedom so as to result in up to two degrees of freedom alignment of the at least one guide for preparing the bone element for the implant,
wherein the third ball head fastener, the fourth ball head fastener and the fifth ball head fastener are working in parallel to perform adjustments in up to three additional degrees of freedom so as to result in up to three additional degrees of freedom alignment of the at least one guide for preparing the bone element for the implant, and
wherein a total degree of freedom adjustment of the at least one guide relative to the first component is up to 5 degrees of freedom.

8. The alignment guide of claim 7 wherein the first component includes at least one bore for accommodating a fastener for removably fixating the first component to the bone element.

9. The alignment guide of claim 7 wherein adjustments are made to control up to five degrees of freedom selected from the group consisting of flexion/extension angle, varus/valgus angle, distal cut resection level, anterior/posterior positioning, internal/external rotation and medio/lateral positioning.

10. The alignment guide of claim 7 wherein the first component further comprises a navigation tracker of a computer-assisted navigation system.

11. The alignment guide of claim 7 wherein the third component further comprises a navigation tracker of a computer-assisted navigation system.

12. The alignment guide of claim 7 wherein orientation and relative displacement of the second component relative to the first component is continuously adjustable to control the two degrees of freedom.

13. The alignment guide of claim 7 wherein orientation and relative displacement of the third component relative to the second component and the first component is continuously adjustable to control up to three additional degrees of freedom.

* * * * *